(12) United States Patent
Oshima et al.

(10) Patent No.: US 11,414,691 B2
(45) Date of Patent: Aug. 16, 2022

(54) ORGANOID WITH METASTATIC PROPERTY AND USE THEREOF

(71) Applicant: National University Corporation Kanazawa University, Kanazawa (JP)

(72) Inventors: Masanobu Oshima, Kanazawa (JP); Mizuho Nakayama, Kanazawa (JP); Eri Sakai, Kanazawa (JP)

(73) Assignee: National University Corporation Kanazawa University, Ishikawa (JP)

( * ) Notice: Subject to any disclaimer, the term of this patent is extended or adjusted under 35 U.S.C. 154(b) by 667 days.

(21) Appl. No.: 16/330,722

(22) PCT Filed: Sep. 7, 2017

(86) PCT No.: PCT/JP2017/032335
§ 371 (c)(1),
(2) Date: Mar. 5, 2019

(87) PCT Pub. No.: WO2018/047914
PCT Pub. Date: Mar. 15, 2018

(65) Prior Publication Data
US 2019/0211372 A1   Jul. 11, 2019

(30) Foreign Application Priority Data

Sep. 8, 2016   (JP) .............................. JP2016-175478
Mar. 14, 2017   (JP) .............................. JP2017-049202

(51) Int. Cl.
| | |
|---|---|
| *C12Q 1/02* | (2006.01) |
| *C12N 5/09* | (2010.01) |
| *C12N 5/071* | (2010.01) |
| *G01N 33/50* | (2006.01) |
| *C12N 5/00* | (2006.01) |

(52) U.S. Cl.
CPC ........... *C12Q 1/025* (2013.01); *C12N 5/0062* (2013.01); *C12N 5/0679* (2013.01); *C12N 5/0693* (2013.01); *G01N 33/5011* (2013.01); *G01N 33/5088* (2013.01); *A01K 2207/12* (2013.01); *C12N 2501/11* (2013.01); *C12N 2501/15* (2013.01); *C12N 2501/727* (2013.01); *C12N 2510/00* (2013.01); *C12N 2513/00* (2013.01); *C12N 2533/54* (2013.01); *C12N 2533/76* (2013.01); *C12N 2533/90* (2013.01)

(58) Field of Classification Search
CPC ................................................ C12N 2533/76
See application file for complete search history.

(56) References Cited

FOREIGN PATENT DOCUMENTS

WO    2015/196012 A1    12/2015

OTHER PUBLICATIONS

Boj, S.F., et al., "Organoid Models of Human and Mouse Ductal Pancreatic Cancer," Cell 160:324-338, Jan. 2015.
The Cancer Genome Atlas Network, "Comprehensive Molecular Portraits of Human Breast Tumours," Nature 490(7418):61-70, Oct. 2012.
Cao, D., et al., "A New Tumorsphere Culture Condition Restores Potentials of Self-Renewal and Metastasis of Primary Neuroblastoma in a Mouse Neuroblastoma Model," PLOS ONE 9(1):e86813, Jan. 2014, pp. 1-8.
Drost, J., et al., "Sequential Cancer Mutations in Cultured Human Intestinal Stem Cells," Nature 521(7550):43-47, May 2015.
Fujii, M., et al., "A Colorectal Tumor Organoid Library Demonstrates Progressive Loss of Niche Factor Requirements During Tumorigenesis," Cell Stem Cell 18:827-838, Jun. 2016.
International Search Report dated Nov. 28, 2017, issued in International Application No. PCT/JP2017/032335, filed Sep. 7, 2017, 4 pages.
Matano, M., et al., "Modeling Colorectal Cancer Using CRISPR-Cas9-Mediated Engineering of Human Intestinal Drganoids," Nature Medicine 21(3):256-262, Mar. 2015.
Ooshima, H., et al., "Carcinogenesis Caused by Genetic Mutation and Interaction of Microenvironment," Experimental Medicine 34(14):2294-2299, Sep. 2016.
O'Rourke, K.P., et al., "Transplantation of Engineered Organoids Enables Rapid Generation of Metastatic Mouse Models of Colorectal Cancer," Nature Biotechnology 35(6):577-582, Jun. 2017.
Weeber, F., et al., "Preserved Genetic Diversity in Organoids Cultured From Biopsies of Human Colorectal Cancer Metastases," Proceedings of the National Academy of Sciences of the United States of America 112(43):13308-13311, Oct. 2015.

*Primary Examiner* — Bin Shen
(74) *Attorney, Agent, or Firm* — Christensen O'Connor Johnson Kindness PLLC

(57) ABSTRACT

Provided are an organoid having a metastatic property when transplanted into an immunocompetent non-human animal of the same species, a cell strain having a metastatic property when transplanted into an immunocompetent non-human animal of the same species, and a non-human animal including the organoid or the cell strain.

2 Claims, 5 Drawing Sheets

Specification includes a Sequence Listing.

(a)

(b)

(a)

(b)

ORGANOID WITH METASTATIC PROPERTY AND USE THEREOF

TECHNICAL FIELD

The present invention relates to an organoid and use thereof.

Priority is claimed on Japanese Patent Application No. 2016-175478, filed on Sep. 8, 2016, Japanese Patent Application No. 2017-049202, filed on Mar. 14, 2017, and National Stage of International Application PCT/JP2017/032335, filed on Sep. 7, 2017 the contents of which are incorporated herein by reference.

BACKGROUND ART

Accumulation of mutations in a plurality of driver genes is required for the development and malignant alteration of colorectal cancer. According to a report from The Cancer Genome Atlas (TCGA) Network, a candidate for a driver gene of colorectal cancer has been elucidated (refer to, for example, NPL 1).

Among them, mutations in each of APC, KRAS, TGFBR2, and P53 genes were detected at high frequency, and these genes are perceived to be important driver genes.

Recently, it has been reported that tumors are formed when human normal intestinal epithelial stem cells are three-dimensionally cultured (also referred to as organoid culture), mutations in each of APC, KRAS, SMAD4, P53, and PIK3CA genes are introduced into these cells, and these cells are transplanted into a NOG (NOD/Shi-scid, IL-2Rγnull) mouse, which is an immunodeficient mouse (refer to, for example, NPLs 2 and 3).

CITATION LIST

Non-Patent Literature

[NPL 1] Cancer Genome Atlas Network., Comprehensive molecular portraits of human breast tumours., Nature, 490 (7418), 61-70, 2012.

[NPL 2] Matano M., et al., Modeling colorectal cancer using CRISPR-Cas9-mediated engineering of human intestinal organoids., Nat. Med., 21(3):256-62, 2015.

[NPL 3] Drost J., et al., Sequential cancer mutations in cultured human intestinal stem cells., Nature., 521 (7550): 43-7, 2015.

SUMMARY OF INVENTION

Technical Problem

However, it is perceived that further changes are required for malignant alteration based on a condition in which even when the organoid into which mutations in each of APC, KRAS, SMAD4, P53, and PIK3CA genes is transplanted into the NOG mouse, no metastasis to other organs is recognized, and cancer does not progress to a complete malignant alteration.

As disclosed in NPLs 2 and 3, it has become possible to reproduce cancer by inserting a driver mutation into a human stem cell organoid by genome editing techniques. Meanwhile, in cancer tissue, an "tumor microenvironment" is formed by a biological response with respect to "cancer cells," and immune cells and stromal cells present therein are known to be involved in the survival and proliferation of cancer cells.

Accordingly, in order to reproduce human carcinogenesis or malignant alteration for cancer research or evaluation research of anticancer drugs, it is necessary to perform experiments of transplanting an organoid into a model animal having a normal immune response, and it is necessary to establish an organoid formed of cells from the same species as the model animal.

An object of the present invention is to provide means for cancer research or evaluation research of anticancer drugs. More specifically, an object is to provide an organoid, a cell strain, a non-human animal, a method for screening of an anticancer drug, a method for producing an organoid, and a method for producing a cell strain.

Solution to Problem

The present invention provides the following aspects.

(1) An organoid having a metastatic property when transplanted into an immunocompetent non-human animal of the same species.

(2) The organoid according to (1), which is derived from a rodent.

(3) The organoid according to (1) or (2), in which APC, KRAS, TP53, and/or TGFBR2 or SMAD4 have mutated.

(4) The organoid according to any one of (1) to (3), in which APC, KRAS, TP53, and TGFBR2 have mutated.

(5) The organoid according to (3) or (4), in which a mutation in the TP53 is a gain-of-function mutation.

(6) The organoid according to any one of (1) to (5) of a receipt number NITE ABP-02345.

(7) A cell strain having a metastatic property when transplanted into an immunocompetent non-human animal of the same species.

(8) The cell strain according to (7), which is derived from a rodent.

(9) The cell strain according to (7) or (8), in which APC, KRAS, TP53, and/or TGFBR2 or SMAD4 have mutated.

(10) The cell strain according to any one of (7) to (9), in which APC, KRAS, TP53, and TGFBR2 have mutated.

(11) The cell strain according to (9) or (10), in which a mutation in the TP53 is a gain-of-function mutation.

(12) The cell strain according to any one of (7) to (11) of a receipt number NITE ABP-02384.

(13) A non-human animal including the organoid according to any one of (1) to (6), or the cell strain according to any one of (7) to (12).

(14) The non-human animal according to (13), which is immunocompetent.

(15) A method for screening of an anticancer drug, including a step of bringing a candidate substance for a cancer therapeutic drug into contact with the organoid according to any one of (1) to (6) or the cell strain according to any one of (7) to (12) to test inhibition of cancer cell proliferation.

(16) A method for screening of an anticancer drug, including a step of administering a candidate substance for a cancer therapeutic drug to the non-human animal according to (13) or (14) to test inhibition of cancer cell proliferation.

(17) A method for producing an organoid having a metastatic property when transplanted into an immunocompetent non-human animal of the same species, the method including a step of three-dimensionally culturing a non-human animal cell in which a driver gene has mutated until the cell acquires metastatic capacity to obtain the organoid.

(18) The method for producing an organoid according to (17), in which the driver genes are APC, KRAS, TP53, and TGFBR2 or SMAD4.

(19) A method for producing a cell strain having a metastatic property when transplanted into an immunocompetent non-human animal of the same species, the method including a step of two-dimensionally culturing the organoid obtained by using the method for producing an organoid according to (17) or (18).

Advantageous Effects of Invention

According to the present invention, it is possible to provide means for cancer research or evaluation research of anticancer drugs. More specifically, it is possible to provide an organoid, a cell strain, a non-human animal, a method for screening of an anticancer drug, and a method for producing an organoid.

DESCRIPTION OF EMBODIMENTS

Figure 1:
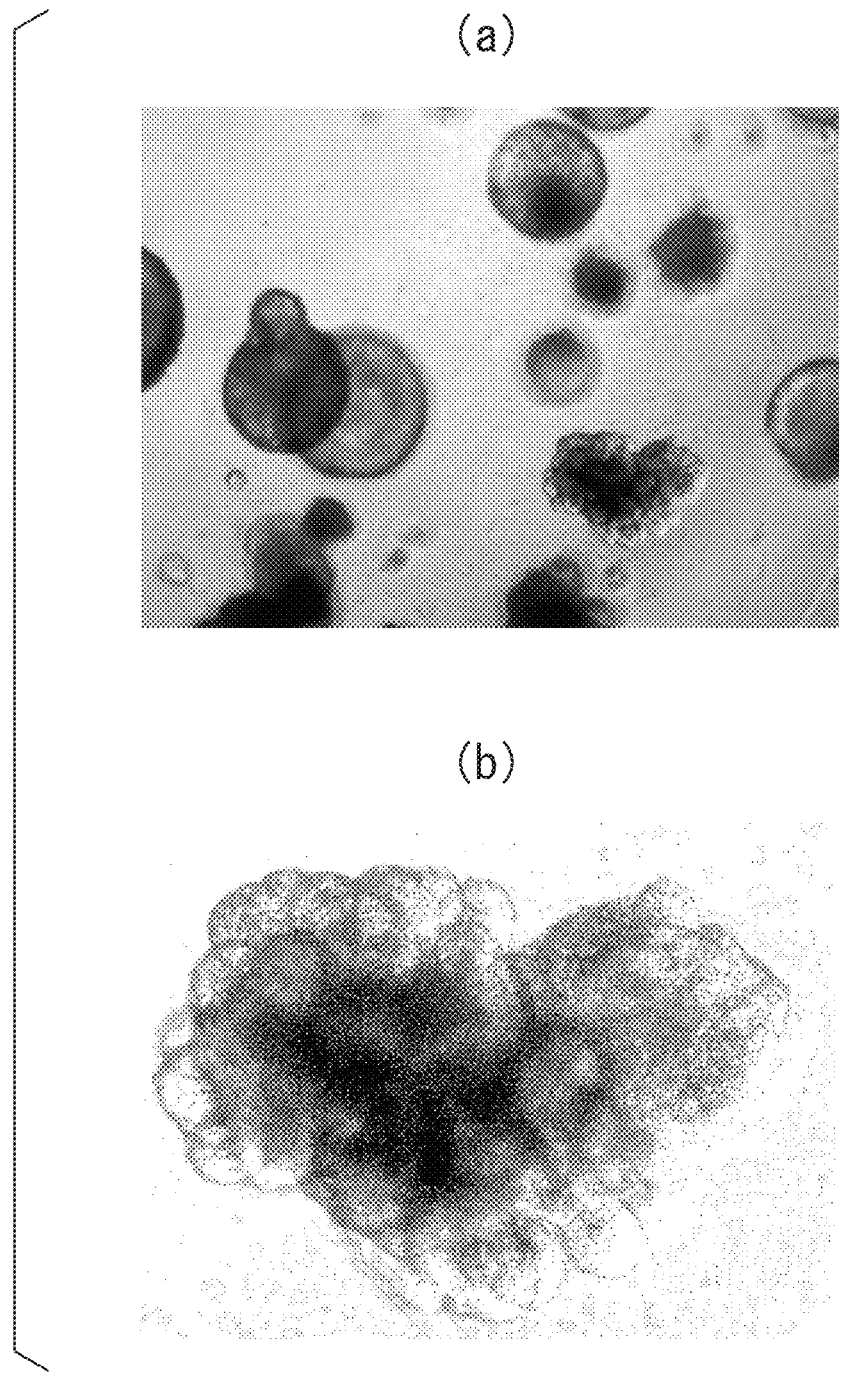
In FIG. 1, (a) is an observation image of an organoid (AKTP-3D) having a metastatic property even under an immunocompetent state. (b) is an observation image of an example of an organoid having a duct-like structure.

[Organoid]
An organoid of the present invention has a metastatic property when transplanted into an immunocompetent non-human animal of the same species. In the present invention, the term "organoid" means a cellular organism in which cells are accumulated and which is close to an organ having a function that cellular tissue originally has.

In the related art, there has been no other means than using an immunodeficient non-human animal such as a NOG mouse as a xenograft model. As will be described later in Examples, the organoid of the present invention has a higher degree of malignancy since the organoid has a metastatic property even under an immunocompetent state. For this reason, according to the organoid of the present invention, it is possible to perform an experiment of transplanting an organoid into a model animal having a normal immune response, such as a C57BL/6 mouse. The organoid of the present invention can be utilized for elucidating growth and development patterns of tumors while considering an immune system, for screening of a therapeutic agent, and the like.

The organoid of the present invention is not particularly limited as long as an organoid is derived from a non-human animal. Examples of non-human animals include cats, dogs, horses, monkeys, cows, sheep, pigs, goats, rabbits, hamsters, guinea pigs, rats, mice, and the like. Among them, from the viewpoint of the achievement of anticancer evaluation, rodents are preferred. Examples of rodents include hamsters, guinea pigs, rats, mice, and the like. Rats and mice are preferred.

The organoid of the present invention preferably contains cells in which a driver gene has mutated. In the present invention, the driver gene refers to a gene that directly plays an important role in the development and progression of cancer, such as a cancer gene and a tumor suppressor gene. Examples of driver genes include KRAS, TP53, APC, TGFBR2, EGF, EGFR, PIK3CA, SMAD4, and the like. In addition, in the present invention, a mutation means that a specific gene or a nucleotide in a chromosomal DNA containing this gene undergoes modification such as substitution, deletion, addition, repetition, inversion, translocation, and the like.

In the organoid of the present invention, it is preferable that APC, KRAS, TP53 and/or TGFBR2 or SMAD4 have mutated. Examples of combinations of mutated driver genes include APC, KRAS, and TP53; APC, KRAS, and TGFBR2; APC, KRAS, and SMAD4; APC, KRAS, TP53, and TGFBR2; and APC, KRAS, TP53, and SMAD4.

Pieces of information on mouse cDNA sequences of APC, KRAS, TP53, TGFBR2, and SMAD4 are described below.
APC NM_007462.3
KRAS NM_021284.6
TP53 NM_001127233.1 NM_011640.3
TGFBR2 NM_009371.3 NM_029575.3
SMAD4 NM_008540.2

A cDNA sequence of an APC gene registered as the above-mentioned GenBank accession number is shown as SEQ ID NO: 1. An amino acid sequence of an APC protein is shown as SEQ ID NO: 2. A cDNA sequence of a KRAS gene is shown as SEQ ID NO: 3. An amino acid sequence of a KRAS protein is shown as SEQ ID NO: 4. cDNA sequences of a TP53 gene are shown as SEQ ID NOs: 5 and 7. Amino acid sequences of a TP53 protein are shown as SEQ ID NOs: 6 and 8. cDNA sequences of a TGFBR2 gene are shown as SEQ ID NOs: 9 and 11. Amino acid sequences of a TGFBR2 protein are shown as SEQ ID NOs: 10 and 12. A cDNA sequence of a SMAD4 gene is shown as SEQ ID NO: 13. An amino acid sequence of a SMAD4 protein is shown as SEQ ID NO: 14.

Examples of mutant-type APCs include an APC in which a translation termination mutation has been introduced in the 716th codon (ApcA716), an APC in which a translation termination mutation has been introduced in the 1638th codon (Apc1638N), and the like, in an amino acid sequence of a mouse. These mutations are preferably a homozygous mutation rather than being a heterozygous mutation.

Examples of mutant-type KRASs include a KRAS in which a base substitution mutation has been introduced in the 12th or 13th codon in an amino acid sequence of a mouse. G12D is preferable.

As a mutant-type TGFBR2 or a mutant-type SMAD4, a deletion mutant-type is preferred. These mutations are preferably a homozygous mutation rather than being a heterozygous mutation. Both factors are present in the same pathway, and therefore it is sufficient as long as any one of the deletion mutations are present.

As a mutant-type TP53, a TP53 having a gain-of-function mutation is preferred. Examples of such mutations include a mutation in which a base substitution mutation has been introduced in the 172th codon (R172H), a mutation in which a base substitution mutation has been introduced in the 270th codon (R270H), or the like in an amino acid sequence of a mouse. It is considered that, due to such a gain-of-function mutation, a mutant-type p53 translocates to the nucleus, induces the expression of a wide range of genes, and causes malignancy in cells. It is considered that a wild-type p53 forms a complex with the mutant-type p53 to inhibit nuclear translocation. Therefore, a mutation in TP53 is preferably a homozygous mutation rather than being a heterozygous mutation. In addition, a wild-type TP53 is preferably deleted due to LOH.

The origin of cells that the organoid of the present invention contains is not particularly limited. It is possible to use cells derived from various types of cancer. Examples of types of cancer include biliary duct cancer, intestinal cancer, lung cancer, stomach cancer, esophageal cancer, breast cancer, bladder cancer, prostate cancer, myeloma, lymphoma, and the like. Intestinal cancer is preferred. In addition, examples of intestinal cancer include cancer derived from intestinal epithelial tissue.

(a) of FIG. 1 is an observation image of an example of an organoid having a metastatic property even under an immunocompetent state. Many organoids show a cyst-like morphology. As shown in (b) of FIG. 1, some of these organoids exhibit a duct-like structure.

The organoid of the present invention is preferably an organoid of a receipt number NITE ABP-02345 (hereinafter referred to as "AKTP-3D organoid" in some cases). This organoid is an organoid established by the inventors of the present invention. As shown in Examples, the present organoid forms tumors and metastasizes to other organs even when transplanted into an immunodeficient NOG mouse or even when transplanted into an immunocompetent C57BL/6 mouse.

The present organoid provides materials for cancer research or evaluation research of anticancer drugs, which takes immunological response into consideration.

[Cell strain]

A cell strain of the present invention has a metastatic property when transplanted into an immunocompetent non-human animal of the same species. As will be described later in Examples, when the cell strain of the present invention is three-dimensionally cultured, an organoid having the same properties as those of the organoid of the present invention is formed. A preferable configuration of the cell strain of the present invention is the same as that of the above-described [Organoid], and therefore explanation thereof will be omitted.

Figure 2:
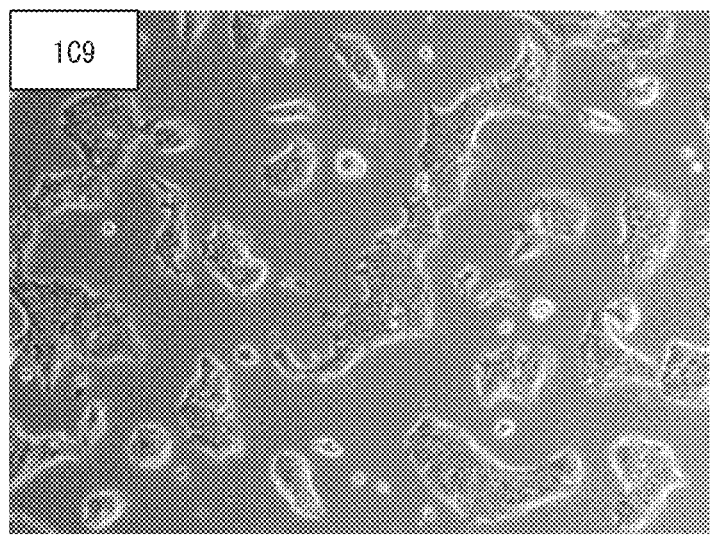
In FIG. 2, (a) is an observation image of a cell strain (AKTP-1C943) having a metastatic property even under an immunocompetent state. (b) is an observation image of a cell strain (AKTP-2A6) having a metastatic property even under an immunocompetent state.
Figure 2:
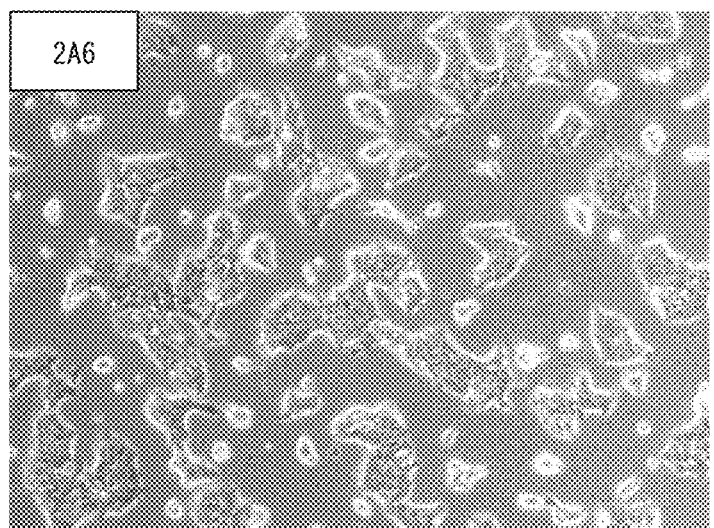

(a) and (b) of FIG. 2 are observation images of a cell strain having a metastatic property even under an immunocompetent state. The cell strain of the present invention is preferably a cell strain of a receipt number NITE ABP-02384 (hereinafter referred to as "AKTP-1C9-β" in some cases). This cell strain is a cell strain established by the inventors of the present invention. As shown in Examples, the present cell strain forms tumors and metastasizes to other organs even when transplanted into an immunodeficient NOG mouse or even when transplanted into an immunocompetent C57BL/6 mouse.

[Non-Human Animal]

A non-human animal of the present invention includes the above-mentioned organoid or cell strain of the present invention. As means for introducing an organoid or cell strain into the non-human animal, transplantation is preferred. A transplantation site is not particularly limited, and examples thereof include a subcutaneous tissue, a spleen, a tail vein, and the like.

Examples of non-human animals include cats, dogs, horses, monkeys, cows, sheep, pigs, goats, rabbits, hamsters, guinea pigs, rats, mice, and the like. Among them, from the viewpoint of the achievement of anticancer evaluation, rodents are preferred. Examples of rodents include hamsters, guinea pigs, rats, mice, and the like. Rats and mice are preferred.

In a case of xenograft transplantation, the non-human animal is preferably immunodeficient. Examples thereof include SCID mice, NOG mice, and the like.

In a case of allograft transplantation, a non-human animal may be immunodeficient or immunocompetent. From a physiological viewpoint, an immunocompetent non-human animal is preferred.

The non-human animal of the present invention can be used as an immunocompetent xenograft model. Therefore, according to the non-human animal of the present invention, materials for cancer research or evaluation research of anticancer drugs, which takes immunological response into consideration, are provided.

In addition, as will be described later in Examples, the non-human animal of the present invention can also be used as a metastasis model, which is an immunocompetent individual, of cancer cells into which only a definite driver gene mutation has been introduced, and thus can be suitably used for evaluation of anticancer drugs.

[Method for Screening of Anticancer Drug]

First Embodiment

In one embodiment, the present invention provides a method for screening of an anticancer drug, which includes a step of bringing a candidate substance for a cancer therapeutic drug into contact with the above-described organoid or cell strain to test inhibition of cancer cell proliferation.

For example, a compound library is added to a medium of the above-described organoid or cell strain to examine influence on cell proliferation. More specifically, for example, the organoid or cell strain is seeded in a well plate and cultured for about 1 to 5 days in the presence of a compound library. Thereafter, for example, the number of viable cells is analyzed by color development due to reduction of a tetrazolium salt. Compounds that inhibit proliferation of the organoid or cell strain are candidates for cancer therapeutic drugs. As a tetrazolium salt, commercially available 3-[4,5-dimethylthiazol-2-yl]-2,5-diphenyltetrazolium bromide (MTT) or the like can be used.

Second Embodiment

In one embodiment, the present invention provides method for screening of an anticancer drug, which includes a step of administering a candidate substance for a cancer therapeutic drug to a non-human animal having the above-described organoid or cell strain to test inhibition of cancer cell proliferation.

For example, the candidate substance for a cancer therapeutic drug is orally or parenterally administered to an immunocompetent mouse into which the organoid or cell strain has been transplanted. Subsequently, inhibition of cancer cell proliferation is tested to confirm effects of the candidate substance for a cancer therapeutic drug. Examples of methods for testing inhibition of cancer cell proliferation include measurement of a size (volume, mass, and the like) of cancer tissue derived from a transplanted organoid or cell strain, and the like. It is highly likely that the candidate substance for a cancer therapeutic drug which reduces the above-mentioned cancer tissue can be utilized as a cancer therapeutic drug.

[Method for Producing Organoid]

A method for producing an organoid of the present invention is a method for producing an organoid having a metastatic property when transplanted into an immunocompetent non-human animal of the same species, the method including a step of three-dimensionally culturing a non-human animal cell in which a driver gene has mutated until the cell acquires metastatic capacity to obtain the organoid.

Examples of driver genes include KRAS, TP53, APC, TGFBR2, EGF, EGFR, PIK3CA, SMAD4, and the like. In the method for producing an organoid of the present invention, it is preferable that APC, KRAS, TP53, and/or TGFBR2 or SMAD4 have mutated, and it is more preferable that APC, KRAS, TP53, and TGFBR2 have mutated.

In addition, as a mutant-type TP53, a TP53 having the gain-of-function mutation described above is preferred.

A method for producing a non-human animal cell in which a driver gene has mutated is not particularly limited. A mutation may be introduced into a driver gene in a cell collected from a non-human animal by using a genome editing method. Examples of genome editing methods include a TALEN system, a Zn finger nuclease system, and a CRISPR-Cas9 system.

In addition, a tumor may be excised from the tissue of the non-human animal in which the driver gene has tissue-specifically mutated, and this tumor may be adjusted by enzymatic treatment with collagenase or the like.

In other words, as one embodiment, the present invention provides a method for producing an organoid having a metastatic property when transplanted into an immunocompetent non-human animal of the same species, the method including Step 1 of excising a tumor from the tissue of the non-human animal in which the driver gene has tissue-specifically mutated to adjust a cell in which the driver genes have mutated; and Step 2 of three-dimensionally culturing the cell until the cell acquires metastatic capacity to obtain the organoid.

Hereinafter, each step will be described in detail.

[Step 1]

As a combination of driver genes having a mutation, a combination of APC, KRAS, TP53, and TGFBR2 is preferable as described above. In order to obtain a non-human animal in which these plurality of driver genes have tissue-specifically mutated, it is preferable to cross non-human animals in which each driver gene has mutated.

In addition, in order to tissue-specifically introduce a mutation, it is preferable to use a non-human animal obtained by crossing a non-human animal which tissue-specifically expresses a site-specific recombination enzyme, with at least one selected from the group consisting of a conditional knockout non-human animal and a conditional transgenic non-human animal.

Examples of conditional knockout non-human animals include a non-human animal having a chromosome in which at least part of a target gene desired to be deleted is sandwiched between site-specific recombination enzyme recognition sequences.

Examples of conditional transgenic non-human animals include a non-human animal having a chromosome containing a gene containing a site-specific recombination enzyme recognition sequence, a transcription termination sequence, the site-specific recombination enzyme recognition sequence from the 5' side in this order, upstream of a target gene having a mutation.

Examples of site-specific recombination enzymes include Cre, Flpe, Dre, and the like. Examples of site-specific enzyme recognition sequences recognized by a site-specific recombination enzyme include loxP, FRT, and rox.

In addition, fusion proteins of a site-specific recombination enzyme and a mutant estrogen receptor (ER) may be used. As an example, a Cre-ER protein is generally present in the cytoplasm, but by binding with tamoxifen, which is an estrogen derivative, the protein migrates into the nucleus and recombines against a loxP sequence. By utilizing the above condition, it is possible to adjust a working time of a Cre-loxP system in a tamoxifen-dependent manner.

Tissue into which a mutation is introduced is not particularly limited. Examples thereof include any tissue such as bile duct, intestine, lung, stomach, esophagus, breast, bladder, and prostate, but intestinal tract is preferable.

[Step 2]

Step 2 is a step of three-dimensionally culturing the cell adjusted in Step 1 until the cell acquires metastatic capacity to obtain an organoid.

In the present invention, the three-dimensional culture refers to a method of culturing cells in the presence of an extracellular matrix. Examples of an extracellular matrix include collagen (type I, type II, type III, type V, type XI, and the like), a basement membrane component (trade name: Matrigel) reconstituted from a mouse EHS tumor extract (including type IV collagen, laminin, heparan sulfate proteoglycan, and the like), glycosaminoglycan, hyaluronic acid, proteoglycan, gelatin, and the like. Matrigel is preferred.

A culture medium used for three-dimensional culture is not particularly limited, and a conventionally known medium is used.

In Step 2, a period for three-dimensional culture is a "period for culturing until acquisition of metastatic property," preferably 3 months or longer, and more preferably 4 months or longer. In order to impart a metastatic property when transplanted into an immunocompetent non-human animal of the same species, not only a mutation of a driver gene but also a secondary change such as an epigenetic change caused by a mutation of a driver gene are perceived to be required.

[Method for Producing Cell Strain]

A method for producing a cell strain of the present invention is a method for producing a cell strain having a metastatic property when transplanted into an immunocompetent non-human animal of the same species, the method including a step of two-dimensionally culturing the organoid obtained by using the above-described method for producing an organoid.

It is possible to establish a cell strain by two-dimensionally culturing the organoid obtained by using the above-described method for producing an organoid, separating the increased cells into a single cell by trypsin treatment or the like, and then cloning the cell.

EXAMPLES

Next, the present invention will be described in more detail by showing experimental examples, but the present invention is not limited to the following experimental examples.

Experimental Example 1

Establishment of Organoid

In order to allow, in an intestinal epithelial cell, deletion or mutation in each mouse gene Apc, Kras, Tgfbr2, and Trp53 corresponding to driver genes APC, KRAS, TGFBR2, and TP53 involved in human colorectal cancer development and malignant alteration, 5 mouse model systems of Apc$^{\Delta 716}$ mice (Oshima. et. al., Proc. Natl. Acad. Sci. USA 92,4482-4486,1995), LSL-KrasG12D mouse (Mouse Repository 01XJ6 NCI-Frederick), Tgfbr2$^{flox}$ mouse (Mouse Repository 01XN5 NCI-Frederick), Trp53$^{LSL\ R270H}$ mouse (Mouse Repository 01XM3 NCI-Frederick), and villin-CreERT2 mouse (el Marjou F. et. al., Genesis 39,186-193,2004) were crossed. Therefore, a mouse in which 4 types of genes other than Tgfbr2 flox were heterozygous and Tgfbr2 flox was homozygous (Apc$_{+/\Delta 716}$, LSL-K-ras$^{G12D}$, Tgfbr2$^{flx/flox}$, Trp53$^{LSL\ R270H}$, and Villin-CreERT2) was produced.

When tamoxifen was administered to this mouse, CreER intestinal-epithelial-cell-specifically migrated to the nucleus, and a flox region on the genome was cut out. Therefore, the genotypes of the intestinal epithelial cell became Apc$^{+/\Delta 716}$, K-ras$^{+/G12D}$, Tgfbr2$^{-/-}$, and Trp53$^{+/R270H}$.

In addition, a normal Apc gene was deleted in the process of cell division. Therefore, the genotypes became APC$^{-/\Delta 716}$, K-ras$^{+/G12D}$, Tgfbr2$^{-/-}$, and Trp53$^{+/R270H}$. By introducing quadruple gene mutations, an invasive bowel tumor was developed.

Tumor tissue generated in this mouse model having quadruple mutations was cut out, treated with collagenase, and then cultured in an Advanced DMEM/F12 medium (3D medium) into which mEGF and mNoggin were added in Matrigel. An organoid was grown to show a cist-like morphology (refer to (a) of FIG. 1). During a period that the organoid was mechanically crushed by pipetting by about one week intervals, transplanted into a new Matrigel, and subcultured for 4 months, part of the organoid changed to a duct-like structure (refer to (b) of FIG. 1). This organoid was deposited at the National Institute of Technology and Evaluation (2-5-8 Kazusa-kamatari, Kisarazu Chiba) (accession number NITE P-02345, cell name "AKTP-3D").

In regard to this organoid, an application has been submitted to the National Institute of Technology and Evaluation for transfer from domestic deposit to international deposit, and received on Aug. 25, 2017 (receipt number: NITE ABP-02345).

A composition of a 3D medium used for culture is shown below.

Advanced DMEM/F12 (ThermoFisher), 1×GlutaMax (Gibco), 10 mM Hepes Buffer (Gibco), 1×N2 Supplement (Gibco), 1×B27 Supplement (Gibco), 1 mM N-Acetylcystein (Gibco), 0.1 µg/ml mNoggin (Peprotech), 0.5 µg/ml mEGF (Invitrogen), and 1×Penicillin/Streptomycin (Wako)

Experimental Example 2

Establishment of Cell Strain

In the same manner as in Experimental Example 1, an organoid obtained by subculturing in three-dimensional culture for 3 months was, on a collagen-coated dish, two-dimensionally cultured in a 3D medium (F3i-3D medium; the above described 3D medium, FBS, A-8301, CHIR99021, and Y-27632) into which FBS and three kinds of inhibitors (a GSK inhibitor, an ALK inhibitor, and a ROCK inhibitor) were added. The increased cells were separated into a single cell by trypsin treatment and then cloned. Therefore, an intestinal epithelial tumor cell strain of a mouse (AKTP-1C9-β and AKTP-2A6) was established. AKTP-1C9-β and AKTP-2A6 were continuously cultured in Advanced DMEM/F12 medium (F3i-Advanced F12 medium; FBS, A-8301, CHIR99021, Y-27632, Advanced DMEM/F12, and Penicillin/Streptomycin) into which FBS and the above-mentioned three kinds of inhibitors were added. (a) and (b) of FIG. 2 are observation images of the established cell strains AKTP-1C9-β and AKTP-2A6, respectively.

These cell strains were deposited at the National Institute of Technology and Evaluation (2-5-8 Kazusa-kamatari, Kisarazu Chiba) (accession number NITE P-02384, cell name "AKTP-1C9-β;" accession number NITE P-02385, cell name "AKTP-2A6").

In regard to this AKTP-1C9-β, an application has been submitted to the National Institute of Technology and Evaluation for transfer from domestic deposit to international deposit, and received on Aug. 25, 2017 (receipt number: NITE ABP-02384). It was confirmed that these cell strains can maintain an epithelial-like structure under three-dimensional culture conditions, such as formation of cyst-like and duct-like organoids in Matrigel.

Experimental Example 3

NOG Mouse into which Organoid was Transplanted

The tumor formation was confirmed when the duct-like organoid obtained after 4 months of culture was subcutaneously transplanted into the NOG mouse.

Figure 3:
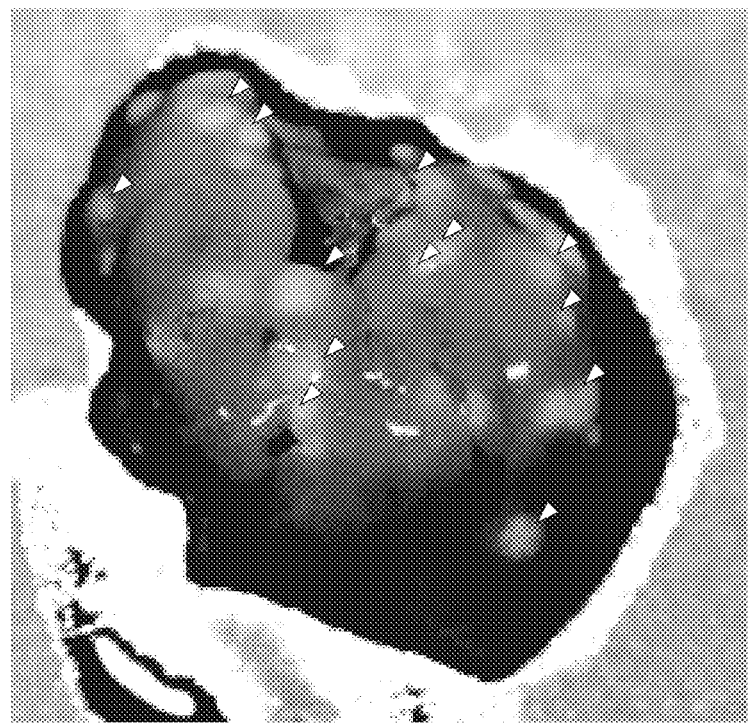
FIG. 3 is an observation image of a liver collected from a NOG mouse into which a duct-like organoid after four months of culture is transplanted.

In addition, when each of the cyst-like organoids obtained immediately after three-dimensional culture and the duct-like organoids obtained after four months of culture were transplanted into the spleen of the NOG mouse, only the latter was confirmed to show metastasis in the liver. The liver collected from the NOG mouse into which the duct-like organoid obtained after four months of culture was transplanted is shown in FIG. 3. In FIG. 3, arrows indicate metastasis points.

Furthermore, when this duct-like organoid was injected into the blood from the tail vein, metastasis to the lung was also confirmed.

A difference in DNA methylation patterns between the cyst-like organoid obtained immediately after three-dimensional culture and the duct-like organoid obtained after 4 months of culture was recognized. Epigenetic change was confirmed to be introduced during 4 months of culture of the organoid.

Experimental Example 4

NOG Mouse into which Intestinal Epithelial Tumor Cell Strain of Mouse was Transplanted Tumor formation was confirmed when the intestinal epithelial tumor cell strain of the mouse (AKTP-1C9-β) established in Experimental Example 2 was subcutaneously transplanted into the NOG mouse.

In addition, when this intestinal epithelial tumor cell strain of the mouse was transplanted into the spleen of the NOG mouse, metastasis to the liver was recognized.

Furthermore, when this intestinal epithelial tumor cell strain of the mouse was injected into the blood from the tail vein, metastasis to the lung was also confirmed.

Experimental Example 5

C57BL/6 Mouse into which Organoid or Intestinal Epithelial Tumor Cell Strain of Mouse was Transplanted When each of the organoid (AKTP-3D) established in Experimental Example 1 and the intestinal epithelial tumor cell strain of the mouse (AKTP-1C9-β) established in Experimental Example 2 was transplanted into the spleen of an immunocompetent C57BL/6 mouse, metastasis to the liver was recognized in both cases.

Figure 4:
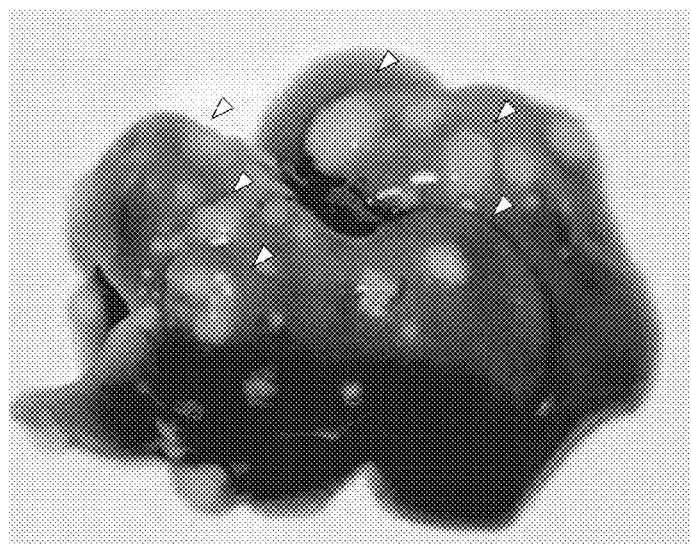
FIG. 4 is an observation image of a liver collected from a C57BL/6 mouse into which the organoid (AKTP-3D) is transplanted.

The liver collected from the C57BL/6 mouse into which the organoid (AKTP-3D) was transplanted is shown in FIG. 4. In FIG. 4, arrows indicate metastasis points. It was confirmed that the organoid or cell strain of the present invention has a metastatic property even under an immunocompetent state. The non-human animal of the present invention can also be used as a metastasis model, which is an immunocompetent mouse, of colorectal cancer cells into which only a definite driver gene mutation has been introduced. Such a metastasis model is unprecedented in the world and can be a very important model for the evaluation of anticancer drugs.

Experimental Example 6

LOH Analysis

Figure 5:
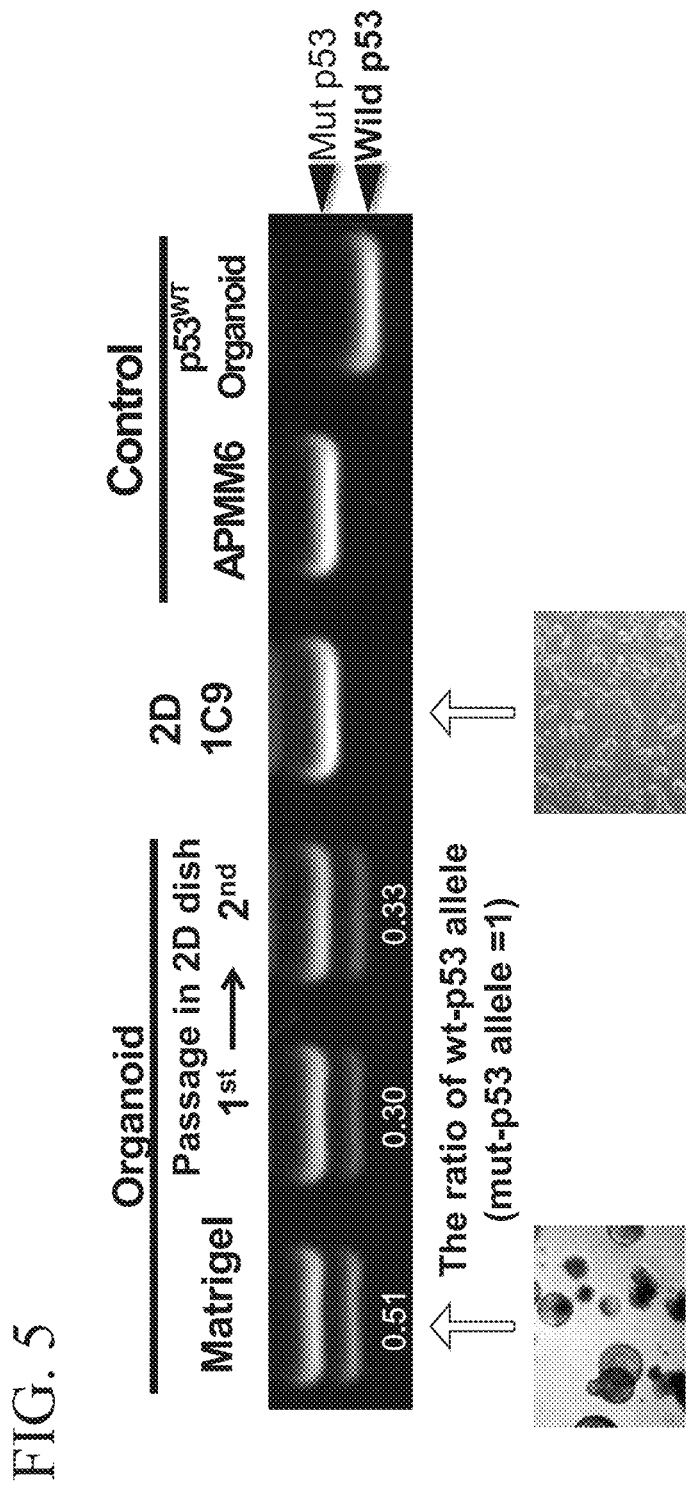
FIG. 5 shows results of LOH analysis on the organoid (AKTP-3D) and an intestinal epithelial tumor cell strain of a mouse (AKTP-1C9-β.

Genomic PCR was performed using the organoid established in Experimental Example 1 (AKTP-3D; denoted as Matrigel in FIG. 5), cells at the first passage (denoted as $1^{st}$ in FIG. 5) and cells at the second passage (denoted as $2^{nd}$ in FIG. 5) which were obtained by two-dimensional culture of this organoid, and the intestinal epithelial tumor cell strain of the mouse established in Experimental Example 2 (AKTP-1C9-β; denoted as 2D1C9 in FIG. 5). The results are shown in FIG. 5. In FIG. 5, numerical values indicate signal intensities of a wild-type Trp53 (denoted as Wild p53 in FIG. 5) when a signal intensity of a mutant-type Trp53 (R270H; denoted as Mut p53 in FIG. 5) was taken as 1.

As shown in FIG. 5, it was confirmed that a ratio of the wild-type Trp53 decreased with each passage of two-dimensional culture. Normal stem cells and benign tumor cells can be cultured by organoid culture, but only cells which acquired cancer cell trait or were immortalized can be passaged in two-dimensional culture. It was confirmed that a Trp53 gene of the organoid (AKTP-3D) established in Experimental Example 1 was heterozygous for R270H/+; however, in a Trp53 gene of the intestinal epithelial tumor cell strain of the mouse established in Experimental Example 2, a wild-type (+) gene was deleted due to LOH.

Experimental Example 7

Soft Agar Colony Assay

Each of the organoid (AKTP-3D) established in Experimental Example 1 and the intestinal epithelial tumor cell strain of the mouse (AKTP-1C9-β; denoted by AKTP-2D in FIG. 6) established in Experimental Example 2 was seeded in agar to be cultured. The number of colonies formed was counted. In addition, a value obtained by dividing the number of colonies formed within the field of view of the same area by using colonies and a cell mass which did not form into a colony as parameters, is denoted as %. The results are shown in FIG. 6.

Figure 6:
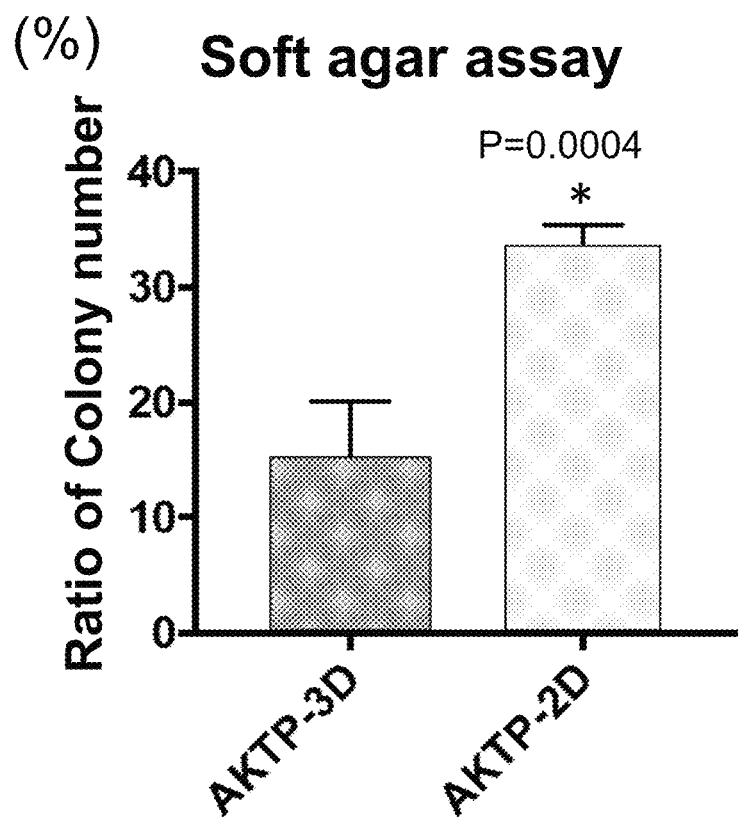
FIG. 6 shows results of a soft agar colony assay on the organoid (AKTP-3D) and the intestinal epithelial tumor cell strain of a mouse (AKTP-1C9-β).

As shown in FIG. 6, it was confirmed that the intestinal epithelial tumor cell strain of the mouse (AKTP-1C9-β) established in Experimental Example 2 has strong tumorigenic properties.

Based on the results of Experimental Examples 6 and 7, it was confirmed that, in the genotypes of the intestinal epithelial tumor cell strain of the mouse established in Experimental Example 2, the wild-type (+) gene was deleted, thereby faithfully realizing human colon cancer cells, and at the same time, acquiring a malignant trait that can be passaged even under two-dimensional culture conditions.

INDUSTRIAL APPLICABILITY

According to the present invention, it is possible to provide means for cancer research or evaluation research of anticancer drugs. More specifically, it is possible to provide an organoid, a cell strain, a non-human animal, a method for screening of an anticancer drug, and a method for producing an organoid.

Accession Number

The organoid (cell name "AKTP-3D") was deposited on National Institute of Technology and Evaluation (2-5-8 Kazusa-kamatari, Kisarazu Chiba) as the "accession number NITE P-02345." In regard to this organoid (cell name "AKTP-3D"), an application has been submitted to the National Institute of Technology and Evaluation for transfer from domestic deposit to international deposit, and received on Aug. 25, 2017 (receipt number: NITE ABP-02345).

The cell strain (cell name "AKTP-1C9-β") was deposited on National Institute of Technology and Evaluation (2-5-8 Kazusa-kamatari, Kisarazu Chiba) as the "accession number NITE P-02384." In regard to this cell strain (cell name "AKTP-1C9-β"), an application has been submitted to the National Institute of Technology and Evaluation for transfer from domestic deposit to international deposit, and received on Aug. 25, 2017 (receipt number: NITE ABP-02384).

The invention claimed is:

1. A cell strain which has a metastatic property when transplanted into an immunocompetent mouse, and is derived from an intestinal epithelial tumor of the mouse, and in which APC, KRAS, TP53, and TGFBR2 have mutated, and a mutation in the TP53 is a gain-of-function mutation,
wherein, in a mutation in the APC, the 716th codon is a translation termination mutation, a normal Apc gene is deleted, and a genotype is APC$^{-/\Delta 716}$,
a mutation in the KRAS is G12D in which a base substitution mutation has been introduced in the 12th codon,
a mutation in the TP53 is R270H, in which a base substitution mutation has been introduced in the 270th codon, and a wild-type (+) gene has been deleted due to Loss of Heterozygosity (LOH), and
a mutation in the TGFBR2 is a homo-deficient mutation, and epigenetic changes have been introduced, and
wherein the cell strain is obtained by two-dimensionally culturing an organoid wherein the organoid has a metastatic property when transplanted into an immunocompetent mouse, and is derived from an intestinal epithelial tumor of the mouse, and in which APC, KRAS, TP53, and TGFBR2 have mutated, and a mutation in the TP53 is a gain-of-function mutation,
wherein, in a mutation in the APC, the 716th codon is a translation termination mutation, a normal Apc gene is deleted, and a genotype is APC$^{-/\Delta 716}$,
a mutation in the KRAS is G12D in which a base substitution mutation has been introduced in the 12th codon,
a mutation in the TP53 is R270H in which a base substitution mutation has been introduced in the 270th codon, and is a heterozygous mutation, and
a mutation in the TGFBR2 is a homo-deficient mutation, in which epigenetic changes have been introduced, and
wherein the organoid is obtained by excising tumor tissue generated from a mouse in which the APC, KRAS, TP53, and TGFBR2 as driver genes intestinal-epithelial-cell-specifically have the mutations, adjusting a cell in which the driver genes have mutated, and three-dimensionally culturing the cell until the cell acquires metastatic capacity,
and deleting the wild type (+) gene of the heterozygous mutation TP53 due to LOH.

2. A cell strain of a receipt number NITE ABP-02384.

* * * * *

SEQUENCE LISTING

```
<160> NUMBER OF SEQ ID NOS: 14

<210> SEQ ID NO 1
<211> LENGTH: 8529
<212> TYPE: DNA
<213> ORGANISM: Mus musculus

<400> SEQUENCE: 1
```

```
atggctgcag cttcatatga tcagttgtta aagcaagttg aggcactgaa gatggagaac    60
tcaaatcttc gacaagagct agaagataat tccaatcatc ttacaaaact ggaaactgag   120
gcatctaata tgaaggaagt acttaagcag ctacagggaa gtattgaaga tgagactatg   180
acttctggac agattgactt actagagcgt cttaaagaat ttaacttaga tagtaatttc   240
cccggagtga aactacgctc aaaaatgtcc cttcgctcct acggaagtcg ggaaggatct   300
gtatccagcc gttcaggaga atgcagtcct gtccccatgg ggtcattccc aagaagaaca   360
tttgtaaatg gaagcagaga gagtactggg tatctagaag agcttgaaaa agaaagatca   420
ttactccttg ctgatcttga caagaagag aaggaaaagg actggtatta tgctcaactt   480
cagaacctca caaaaagaat agatagcctg cctttaactg aaaattttc cttacagaca   540 gacatgacaa gacggcagct ggagtatgaa gcaaggcaga tcagggctgc aatggaggag   600
cagcttggca cctgccagga catggagaag cgtgcacagc gaagaatagc caggatccag   660
caaatagaaa aggacatact gcgcgtgcgc cagcttttac agtcccaggc ggcggaagcg   720
gagaggtcat ctcagagcag gcatgatgct gcctcccatg aagctggccg gcagcacgaa   780
ggccacggag tggcagaaag caacaccgca gcctccagta gtggtcagag tccagctaca   840
cgtgtggatc acgaaacagc cagtgttttg agttctagcg gcacgcactc tgctcctcga   900
aggttgacaa gtcatctggg gacaaaggtg gaaatggtgt attccttgtt gtcaatgctt   960
ggtactcatg ataaggacga tatgtcacga actttgctag ctatgtccag ctcccaagac  1020
agctgtatat ccatgcggca gtctggatgt cttcctctcc tcatccagct tttacatggc  1080
aatgacaaag actctgtatt gttgggaaat tcccggggca gtaaagaggc tcgggccagg  1140
gccagtgcag cactccacaa catcattcac tcacagcctg atgacaagag aggcaggcgt  1200
gaaatccgag tccttcatct tttggaacag atacagagctt actgtgaaac ctgttgggag  1260
tggcaggaag cccacgaaca aggcatggac caggacaaaa acccaatgcc agctcctgtt  1320
gagcatcaga tctgtcctgc tgtgtgtgtt ctaatgaagc tttcatttga tgaagagcat  1380
aggcatgcaa tgaatgaact gggggactg caggccattg cagagttatt gcaggtggac  1440
tgtgagatgt atgggcttac taatgaccac tacagtgtta ctttaagacg gtatgctgga  1500
atggctttga caaacttgac cttttggagat gttgccaaca aggctacgct gtgttctatg  1560
aaaggctgca tgagagcact tgtggcccag ttaaaatctg agagtgaaga cttacagcag  1620
gttattgcaa gtgttttgag gaatttgtct tggcgagcag atgtaaatag caaaaagacg  1680
ttgagagaag ttggaagtgt gaaagcattg atggaatgtg cttttgaagt taaaaaggaa  1740
tcaaccctca aaagcgtttt gagtgcctta tggaacctgt ctgcacactg cactgagaat  1800
aaggctgaca tctgtgctgt ggatggagca ctggcatttc tggttggcac cctcacttac  1860
cggagccaga caaatacttt agccattatt gaaagtggag gtgggatatt acggaatgtg  1920
tccagcttga tagctacaaa cgaagaccac aggcaaatcc taagagagaa caattgccta  1980
caaactttat tacagcactt gaaatctcac agcttgacaa tagtcagtaa tgcatgtgga  2040
actttgtgga atctctcagc aagaaatcct aaagaccagg aagccttgtg ggacatgggg  2100
gcagtgagca tgctcaagaa cctcattcat tccaagcaca aaatgattgc catgggaagt  2160
gcagcagctt aaggaatctc atggcaaac agacctgcaa agtataagga tgccaatatc  2220
atgtctcccg gctcaagtct gccatccctt cacgttagga acagaaagc tctagaagct  2280 gagctagatg ctcagcattt atcagaaacc ttcgacaaca ttgacaacct aagtcccaag  2340
gcctctcacc ggagtaagca gagacacaag cagaatcttt atggtgacta tgcttttgac  2400
```

```
gccaatcgac atgatgatag taggtcagac aatttcaata ctggaaacat gactgttctt   2460
tcaccatatt taaatactac ggtattgccc agctcttctt cctcaagggg aagtttagac   2520
agttctcgtt ctgagaaaga cagaagtttg gagagagagc gaggtattgg cctcagtgct   2580
taccatccaa caacagaaaa tgcaggaacc tcatcaaaac gaggtctgca gatcactacc   2640
actgcagccc agatagccaa agttatggaa gaagtatcag ccattcatac ctcccaggac   2700
gacagaagtt ctgcttctac caccgagttc cattgtgtgg cagacgacag gagtgcggca   2760
cgaagaagct ctgcctccca cacacactca aacacataca acttcactaa gtcggaaaat   2820
tcaaatagga catgctctat gccttatgcc aaagtggaat ataaacgatc ttcaaatgac   2880
agtttaaata gtgtcactag tagtgatgga tatggtaaaa gaggccaaat gaaaccctca   2940
gttgaatcct attctgaaga tgatgaaagt aaattttgca gttatggtca gtatccagct   3000
gacctagccc ataagataca cagtgcaaat catatggatg ataatgatgg agaactggat   3060
acaccaataa attacagtct taaatattca gatgagcagt tgaactcagg aaggcagagt   3120
ccctcacaga atgaaaggtg ggcaagacca aagcatgtga tagaagatga aataaagcaa   3180
aacgagcaaa gacaagcaag aagccagaac accagttatc ctgtctattc tgagaatacc   3240
gatgacaaac acctcaaatt ccaaccacat tttggacaac aagaatgtgt tccccatat    3300 aggtcaaggg gaaccagtgg ttcagaaaca aatcgaatgg gttctagtca tgcaattaat   3360
caaaatgtaa accagtctct gtgtcaggaa gatgattatg aagatgataa acctaccaac   3420
tacagtgaac gttattctga ggaagaacaa catgaagaag aagaagagag accgacaaat   3480
tatagcataa aatataatga agagaaacat catgtggatc agcctattga ttatagttta   3540
aaatatgcca ctgacatttc ttcctcacaa aaaccatcat ttcattctc aaagaattca    3600 tcagcacaaa gcactaaacc tgaacatctc tctccaagca gcgagaatac agctgtacct   3660
ccatctaatg ccaaaaggca gaatcagctg cgtccaagtt cagcacaaag aaatggccag   3720
actcaaaaag gcactacttg caaagtcccc tccatcaacc aagaaacaat acagacttac   3780
tgcgtagaag acaccccaat atgttttca aggtgcagtt cattatcatc actgtcatca     3840
gctgacgatg aaataggatg tgatcagaca acacaggaag cagattctgc taatactctg   3900
cagacagcag aagtaaaaga gaatgatgta actcggtcag ctgaagatcc tgcaactgaa   3960
gttccagcag tgtcccagaa tgctagagcc aaacccagcc gactccaggc ttctggctta   4020
tcttcagaat caaccaggca taataaagct gttgagtttt cttcaggagc caagtctccc   4080
tccaaaagtg gtgctcagac acccaaaagt cccccagaac actatgtcca ggagactccg   4140
ctcgtattca gcaggtgtac ttctgtcagc tcccttgaca gttttgagag tcgctccatt   4200
gccagctctg ttcagagtga gccatgtagt ggaatggtga gtggcatcat aagcccagt    4260 gaccttccag atagtcctgg gcagaccatg ccaccaagca gaagcaaaac ccctccacct   4320
cctcacagaa cagtgcaggc caagagagag gtgccaaaaa gtaaagtccc tgctgctgag   4380
aagagagaga gtgggcctaa gcagactgct gtaaatgctg ccgtgcagag ggtgcaggtc   4440
cttccagacg tggatacttt gttacacttc gccacagaaa gtactccaga cgggttttct   4500
tgttcctcca gcctaagtgc tctgagcctg atgagccatt tatacagaa agatgtagaa     4560 ttaagaatca tgcctccagt tcaggaaaac gacaatggga atgaaactga atcagaacag   4620
cctgaggaat caaatgaaaa accaggataaa gaggtagaaa agcctgactc tgaaaaagac   4680
ttattagatg attctgatga cgatgatatt gaaatattag aagaatgtat tatttcagcc   4740
```

```
atgccaacaa agtcatcacg caaagccaaa aaactagccc agactgcttc aaaattacct    4800
ccacctgtgg caaggaaacc aagtcagcta cctgtgtata aacttctgcc agcacagaat    4860
aggctgcagg cacaaaaaca tgttagcttt acaccagggg atgatgtgcc ccgggtgtac    4920
tgtgtagaag ggacacctat aaacttttcc acagcaacgt ctctaagtga tctgacaata    4980
gagtcccctc caaatgaatt ggctactgga gatggggtca gagcgggtat acagtcaggt    5040
gaatttgaaa acgagatac cattcctaca gaaggcagaa gtacagatga tgctcagcga    5100
ggaaaaatct catctatagt tacaccagac ctggatgaca caaagcaga ggaaggagat    5160 attcttgcag aatgtatcaa ttctgctatg cccaaaggaa aaagccacaa gcctttccga    5220
gtgaaaaaga taatggacca agtccaacaa gcatcctcga cttcatctgg agctaacaaa    5280
aatcaagtag acactaagaa aaagaagcct acttcaccag taaagcccat gcccacaaaat    5340 actgaatata aacgcgtgt gagaaagaat acagactcaa aagttaatgt aaatactgaa    5400
gaaactttct cagacaacaa agactcaaag aaaccaagct acaaaccaa tgccaaggcc    5460 ttcaatgaaa agctacctaa caatgaagac agagtgcggg ggagcttcgc cttggactca    5520
ccgcatcact acacccctat tgaggggacg ccgtactgct tttcccgaaa tgactccttg    5580
agttctctgg attttgatga tgacgatgtt gacctttcca gggaaaaggc cgagttaaga    5640
aagggcaaag aaagcaagga ttccgaagcc aaagttacct gccgcccaga accaaactca    5700
agccagcagg cagctagtaa gtcacaagcc agtataaaac atccagcaaa cagagcacag    5760
tccaaaccag tgctgcagaa acagcccact tttccccagt cctccaaaga cggaccagat    5820
agaggggcag caactgacga aaaactgcag aattttgcta ttgaaaatac tccagtttgc    5880
ttttctcgaa attcctctct gagttccctt agtgacattg accaggaaaa caacaataac    5940
aaagaaagtg aaccaatcaa agaagctgaa cctgccaact cacaaggaga gcccagtaag    6000
cctcaggcat ccgggtatgc tcccaagtcc ttccacgtcg aagacacccc tgtctgtttc    6060
tcaagaaaca gctctctcag ttctcttagc attgactctg aggacgacct gttacaggag    6120
tgtataagtt ctgccatgcc aaaaaagaaa aggccttcaa gactcaagag tgagagcgaa    6180
aagcagagcc ctagaaaagt gggtggcata ttagctgaag acctgacgct tgatttgaaa    6240
gatctacaga ggccagattc agaacacgct ttctcccccg actcagaaaa ttttgactgg    6300
aaagctattc aggaaggcgc aaactccata gtaagtagtt tgcaccaagc tgctgcagcc    6360
gccgcgtgct tatctagaca agcgtcatcc gactcagatt ccattctgtc actaaagtcc    6420
ggcatttctc tgggatcgcc ttttcatctt acacctgatc aagaggaaaa gccattcaca    6480
agcaataaag gcccaagaat tctcaaacct ggagagaaaa gcacattaga agcaaaaaaa    6540
atagaatctg aaaacaaagg aatcaaaggc gggaaaaagg tttataaaag cttgattacg    6600
ggaaagattc gctccaattc agaaatttcc agccaaatga acaacccct cccgacaaac    6660 atgccttcaa tctcaagagg caggacgatg attcacatcc cagggcttcg gaatagctcc    6720
tctagtacaa gccctgtctc taagaaaggc ccaccccctca agactccagc ctctaaaagc    6780
cccagtgaag ggccgggagc taccacttct cctcgaggaa ctaagccagc aggaaagtca    6840
gagcttagcc ctatcaccag gcaaacttcc caaatcagtg ggtcaaataa ggggtcttct    6900
agatcaggat ctagagactc cactccctca agacctacac agcaaccatt aagtaggcca    6960
atgcagtctc cagggcgaaa ctcaattttc cctggtagaa atggaataag ccctcctaac    7020
aaactgtctc agctgcccag aacatcatct cccagtactg cttcaactaa gtcctccggt    7080
tctgggaaaa tgtcatatac atccccaggt agacagctga gccaacaaaa tcttaccaaa    7140
```

-continued

```
caagcaagtt tatccaagaa tgccagcagt atccccagaa gtgagtcggc atctaaagga    7200
ctgaatcaga tgagtaacgg caatgggtca aataaaaagg tagaactttc tagaatgtct    7260
tcaactaaat caagtggaag tgaatcagac agatcagaaa ggcctgcatt agtacgccag    7320
tctactttca tcaaagaagc ccccaagccca accctgagga ggaaactgga ggaatctgcc    7380
tcatttgaat ccctttctcc atcttctaga ccagattctc ccaccaggtc gcaggcacag    7440
accccagttt taagcccttc ccttcctgat atgtctctgt ccacacatcc atctgttcag    7500
gcaggtgggt ggcgaaagct cccgcctaat ctcagcccca ctatcgagta taatgacgga    7560
aggcccacaa aacggcatga tattgcacgc tcccattctg aaagtccttc cagactacca    7620
atcaaccggg cgggaacctg gaagcgtgaa cacagcaaac attcctcgtc ccttcctcga    7680
gtgagtactt ggaagaagaac tggaagctca tcttctattc tttctgcttc atcagagtcc    7740
agtgaaaaag caaaaagtga ggatgaaagg catgtgagct ccatgccagc acccagacag    7800
atgaaggaaa accaggtgcc caccaaagga acatggagga aaatcaagga aagtgacatt    7860
tctcccacag gcatggcttc tcagagcgct tcctcaggtg ctgccagtgg tgctgaatcc    7920
aagcctctga tctatcagat ggcacctcct gtctctaaaa cagaggatgt ttgggtgaga    7980
attgaggact gccccattaa caaccctaga tctggacggt ccccacagg caacacccc     8040 ccagtgattg acagtgtttc agagaaggga agttcaagca ttaaagattc aaaagacacc    8100
catgggaaac agagtgtggg cagtggcagt cctgtgcaaa ccgtgggtct ggaaacccgc    8160
ctcaactcct tgttcaggt agaggcccca gaacagaaag gaactgaggc aaaaccagga    8220
cagagtaacc cagtctctat agcagagact gctgagacgt gtatagcaga gcgtacccct    8280
ttcagttcca gtagctccag caagcacagc tcacctagcg ggactgttgc tgccagagtg    8340 acaccttta attacaaccc tagccctagg aagagcagcg cagacagcac ttcagcccgg    8400
ccgtctcaga tccctacgcc agtgagcacc aacacgaaga agagagattc gaagactgac    8460
agcacagaat ccagtggagc ccaaagtcct aaacgccatt ccgggtctta cctcgtgacg    8520
tctgttttaa                                                          8529
```

<210> SEQ ID NO 2
<211> LENGTH: 2842
<212> TYPE: PRT
<213> ORGANISM: Mus musculus

<400> SEQUENCE: 2

```
Met Ala Ala Ala Ser Tyr Asp Gln Leu Leu Lys Gln Val Glu Ala Leu
1               5                   10                  15

Lys Met Glu Asn Ser Asn Leu Arg Gln Glu Leu Glu Asp Asn Ser Asn
            20                  25                  30

His Leu Thr Lys Leu Glu Thr Glu Ala Ser Asn Met Lys Glu Val Leu
        35                  40                  45

Lys Gln Leu Gln Gly Ser Ile Glu Asp Glu Thr Met Thr Ser Gly Gln
    50                  55                  60

Ile Asp Leu Leu Glu Arg Leu Lys Glu Phe Asn Leu Asp Ser Asn Phe
65                  70                  75                  80

Pro Gly Val Lys Leu Arg Ser Lys Met Ser Leu Arg Ser Tyr Gly Ser
                85                  90                  95

Arg Glu Gly Ser Val Ser Ser Arg Ser Gly Glu Cys Ser Pro Val Pro
            100                 105                 110

Met Gly Ser Phe Pro Arg Arg Thr Phe Val Asn Gly Ser Arg Glu Ser
```

```
            115                 120                 125
Thr Gly Tyr Leu Glu Glu Leu Glu Lys Glu Arg Ser Leu Leu Leu Ala
        130                 135                 140
Asp Leu Asp Lys Glu Glu Lys Glu Lys Asp Trp Tyr Tyr Ala Gln Leu
145                 150                 155                 160
Gln Asn Leu Thr Lys Arg Ile Asp Ser Leu Pro Leu Thr Glu Asn Phe
                165                 170                 175
Ser Leu Gln Thr Asp Met Thr Arg Arg Gln Leu Glu Tyr Glu Ala Arg
            180                 185                 190
Gln Ile Arg Ala Ala Met Glu Glu Gln Leu Gly Thr Cys Gln Asp Met
        195                 200                 205
Glu Lys Arg Ala Gln Arg Arg Ile Ala Arg Ile Gln Gln Ile Glu Lys
    210                 215                 220
Asp Ile Leu Arg Val Arg Gln Leu Leu Gln Ser Gln Ala Ala Glu Ala
225                 230                 235                 240
Glu Arg Ser Ser Gln Ser Arg His Asp Ala Ala Ser His Glu Ala Gly
                245                 250                 255
Arg Gln His Glu Gly His Gly Val Ala Glu Ser Asn Thr Ala Ala Ser
            260                 265                 270
Ser Ser Gly Gln Ser Pro Ala Thr Arg Val Asp His Glu Thr Ala Ser
        275                 280                 285
Val Leu Ser Ser Ser Gly Thr His Ser Ala Pro Arg Arg Leu Thr Ser
    290                 295                 300
His Leu Gly Thr Lys Val Glu Met Val Tyr Ser Leu Leu Ser Met Leu
305                 310                 315                 320
Gly Thr His Asp Lys Asp Met Ser Arg Thr Leu Leu Ala Met Ser
                325                 330                 335
Ser Ser Gln Asp Ser Cys Ile Ser Met Arg Gln Ser Gly Cys Leu Pro
            340                 345                 350
Leu Leu Ile Gln Leu Leu His Gly Asn Asp Lys Asp Ser Val Leu Leu
        355                 360                 365
Gly Asn Ser Arg Gly Ser Lys Glu Ala Arg Ala Arg Ala Ser Ala Ala
    370                 375                 380
Leu His Asn Ile Ile His Ser Gln Pro Asp Asp Lys Arg Gly Arg Arg
385                 390                 395                 400
Glu Ile Arg Val Leu His Leu Leu Glu Gln Ile Arg Ala Tyr Cys Glu
                405                 410                 415
Thr Cys Trp Glu Trp Gln Glu Ala His Glu Gln Gly Met Asp Gln Asp
            420                 425                 430
Lys Asn Pro Met Pro Ala Pro Val Glu His Gln Ile Cys Pro Ala Val
        435                 440                 445
Cys Val Leu Met Lys Leu Ser Phe Asp Glu Glu His Arg His Ala Met
    450                 455                 460
Asn Glu Leu Gly Gly Leu Gln Ala Ile Ala Glu Leu Leu Gln Val Asp
465                 470                 475                 480
Cys Glu Met Tyr Gly Leu Thr Asn Asp His Tyr Ser Val Thr Leu Arg
                485                 490                 495
Arg Tyr Ala Gly Met Ala Leu Thr Asn Leu Thr Phe Gly Asp Val Ala
            500                 505                 510
Asn Lys Ala Thr Leu Cys Ser Met Lys Gly Cys Met Arg Ala Leu Val
        515                 520                 525
Ala Gln Leu Lys Ser Glu Ser Glu Asp Leu Gln Gln Val Ile Ala Ser
    530                 535                 540
```

-continued

```
Val Leu Arg Asn Leu Ser Trp Arg Ala Asp Val Asn Ser Lys Lys Thr
545                 550                 555                 560

Leu Arg Glu Val Gly Ser Val Lys Ala Leu Met Glu Cys Ala Leu Glu
            565                 570                 575

Val Lys Lys Glu Ser Thr Leu Lys Ser Val Leu Ser Ala Leu Trp Asn
                580                 585                 590

Leu Ser Ala His Cys Thr Glu Asn Lys Ala Asp Ile Cys Ala Val Asp
        595                 600                 605

Gly Ala Leu Ala Phe Leu Val Gly Thr Leu Thr Tyr Arg Ser Gln Thr
610                 615                 620

Asn Thr Leu Ala Ile Ile Glu Ser Gly Gly Ile Leu Arg Asn Val
625                 630                 635                 640

Ser Ser Leu Ile Ala Thr Asn Glu Asp His Arg Gln Ile Leu Arg Glu
            645                 650                 655

Asn Asn Cys Leu Gln Thr Leu Leu Gln His Leu Lys Ser His Ser Leu
                660                 665                 670

Thr Ile Val Ser Asn Ala Cys Gly Thr Leu Trp Asn Leu Ser Ala Arg
        675                 680                 685

Asn Pro Lys Asp Gln Glu Ala Leu Trp Asp Met Gly Ala Val Ser Met
690                 695                 700

Leu Lys Asn Leu Ile His Ser Lys His Lys Met Ile Ala Met Gly Ser
705                 710                 715                 720

Ala Ala Ala Leu Arg Asn Leu Met Ala Asn Arg Pro Ala Lys Tyr Lys
            725                 730                 735

Asp Ala Asn Ile Met Ser Pro Gly Ser Ser Leu Pro Ser Leu His Val
                740                 745                 750

Arg Lys Gln Lys Ala Leu Glu Ala Glu Leu Asp Ala Gln His Leu Ser
        755                 760                 765

Glu Thr Phe Asp Asn Ile Asp Asn Leu Ser Pro Lys Ala Ser His Arg
770                 775                 780

Ser Lys Gln Arg His Lys Gln Asn Leu Tyr Gly Asp Tyr Ala Phe Asp
785                 790                 795                 800

Ala Asn Arg His Asp Asp Ser Arg Ser Asp Asn Phe Asn Thr Gly Asn
            805                 810                 815

Met Thr Val Leu Ser Pro Tyr Leu Asn Thr Thr Val Leu Pro Ser Ser
                820                 825                 830

Ser Ser Ser Arg Gly Ser Leu Asp Ser Ser Arg Ser Glu Lys Asp Arg
        835                 840                 845

Ser Leu Glu Arg Glu Arg Gly Ile Gly Leu Ser Ala Tyr His Pro Thr
850                 855                 860

Thr Glu Asn Ala Gly Thr Ser Ser Lys Arg Gly Leu Gln Ile Thr Thr
865                 870                 875                 880

Thr Ala Ala Gln Ile Ala Lys Val Met Glu Glu Val Ser Ala Ile His
            885                 890                 895

Thr Ser Gln Asp Asp Arg Ser Ser Ser Thr Thr Glu Phe His Cys
                900                 905                 910

Val Ala Asp Asp Arg Ser Ala Ala Arg Arg Ser Ser Ala Ser His Thr
        915                 920                 925

His Ser Asn Thr Tyr Asn Phe Thr Lys Ser Glu Asn Ser Asn Arg Thr
930                 935                 940

Cys Ser Met Pro Tyr Ala Lys Val Glu Tyr Lys Arg Ser Ser Asn Asp
945                 950                 955                 960
```

```
Ser Leu Asn Ser Val Thr Ser Ser Asp Gly Tyr Gly Lys Arg Gly Gln
            965                 970                 975

Met Lys Pro Ser Val Glu Ser Tyr Ser Glu Asp Asp Glu Ser Lys Phe
            980                 985                 990

Cys Ser Tyr Gly Gln Tyr Pro Ala Asp Leu Ala His Lys Ile His Ser
            995                 1000                1005

Ala Asn His Met Asp Asp Asn Asp Gly Glu Leu Asp Thr Pro Ile
    1010                1015                1020

Asn Tyr Ser Leu Lys Tyr Ser Asp Glu Gln Leu Asn Ser Gly Arg
    1025                1030                1035

Gln Ser Pro Ser Gln Asn Glu Arg Trp Ala Arg Pro Lys His Val
    1040                1045                1050

Ile Glu Asp Glu Ile Lys Gln Asn Glu Gln Arg Gln Ala Arg Ser
    1055                1060                1065

Gln Asn Thr Ser Tyr Pro Val Tyr Ser Glu Asn Thr Asp Asp Lys
    1070                1075                1080

His Leu Lys Phe Gln Pro His Phe Gly Gln Glu Cys Val Ser
    1085                1090                1095

Pro Tyr Arg Ser Arg Gly Thr Ser Gly Ser Glu Thr Asn Arg Met
    1100                1105                1110

Gly Ser Ser His Ala Ile Asn Gln Asn Val Asn Gln Ser Leu Cys
    1115                1120                1125

Gln Glu Asp Asp Tyr Glu Asp Asp Lys Pro Thr Asn Tyr Ser Glu
    1130                1135                1140

Arg Tyr Ser Glu Glu Glu Gln His Glu Glu Glu Glu Arg Pro
    1145                1150                1155

Thr Asn Tyr Ser Ile Lys Tyr Asn Glu Glu Lys His His Val Asp
    1160                1165                1170

Gln Pro Ile Asp Tyr Ser Leu Lys Tyr Ala Thr Asp Ile Ser Ser
    1175                1180                1185

Ser Gln Lys Pro Ser Phe Ser Phe Ser Lys Asn Ser Ser Ala Gln
    1190                1195                1200

Ser Thr Lys Pro Glu His Leu Ser Pro Ser Ser Glu Asn Thr Ala
    1205                1210                1215

Val Pro Pro Ser Asn Ala Lys Arg Gln Asn Gln Leu Arg Pro Ser
    1220                1225                1230

Ser Ala Gln Arg Asn Gly Gln Thr Gln Lys Gly Thr Thr Cys Lys
    1235                1240                1245

Val Pro Ser Ile Asn Gln Glu Thr Ile Gln Thr Tyr Cys Val Glu
    1250                1255                1260

Asp Thr Pro Ile Cys Phe Ser Arg Cys Ser Ser Leu Ser Ser Leu
    1265                1270                1275

Ser Ser Ala Asp Asp Glu Ile Gly Cys Asp Gln Thr Thr Gln Glu
    1280                1285                1290

Ala Asp Ser Ala Asn Thr Leu Gln Thr Ala Glu Val Lys Glu Asn
    1295                1300                1305

Asp Val Thr Arg Ser Ala Glu Asp Pro Ala Thr Glu Val Pro Ala
    1310                1315                1320

Val Ser Gln Asn Ala Arg Ala Lys Pro Ser Arg Leu Gln Ala Ser
    1325                1330                1335

Gly Leu Ser Ser Glu Ser Thr Arg His Asn Lys Ala Val Glu Phe
    1340                1345                1350

Ser Ser Gly Ala Lys Ser Pro Ser Lys Ser Gly Ala Gln Thr Pro
```

-continued

```
                1355                1360                1365
Lys Ser Pro Pro Glu His Tyr Val Gln Glu Thr Pro Leu Val Phe
    1370                1375                1380

Ser Arg Cys Thr Ser Val Ser Ser Leu Asp Ser Phe Glu Ser Arg
    1385                1390                1395

Ser Ile Ala Ser Ser Val Gln Ser Glu Pro Cys Ser Gly Met Val
    1400                1405                1410

Ser Gly Ile Ile Ser Pro Ser Asp Leu Pro Asp Ser Pro Gly Gln
    1415                1420                1425

Thr Met Pro Pro Ser Arg Ser Lys Thr Pro Pro Pro Pro Pro Gln
    1430                1435                1440

Thr Val Gln Ala Lys Arg Glu Val Pro Lys Ser Lys Val Pro Ala
    1445                1450                1455

Ala Glu Lys Arg Glu Ser Gly Pro Lys Gln Thr Ala Val Asn Ala
    1460                1465                1470

Ala Val Gln Arg Val Gln Val Leu Pro Asp Val Asp Thr Leu Leu
    1475                1480                1485

His Phe Ala Thr Glu Ser Thr Pro Asp Gly Phe Ser Cys Ser Ser
    1490                1495                1500

Ser Leu Ser Ala Leu Ser Leu Asp Glu Pro Phe Ile Gln Lys Asp
    1505                1510                1515

Val Glu Leu Arg Ile Met Pro Pro Val Gln Glu Asn Asp Asn Gly
    1520                1525                1530

Asn Glu Thr Glu Ser Glu Gln Pro Glu Glu Ser Asn Glu Asn Gln
    1535                1540                1545

Asp Lys Glu Val Glu Lys Pro Asp Ser Glu Lys Asp Leu Leu Asp
    1550                1555                1560

Asp Ser Asp Asp Asp Asp Ile Glu Ile Leu Glu Glu Cys Ile Ile
    1565                1570                1575

Ser Ala Met Pro Thr Lys Ser Ser Arg Lys Ala Lys Lys Leu Ala
    1580                1585                1590

Gln Thr Ala Ser Lys Leu Pro Pro Pro Val Ala Arg Lys Pro Ser
    1595                1600                1605

Gln Leu Pro Val Tyr Lys Leu Leu Pro Ala Gln Asn Arg Leu Gln
    1610                1615                1620

Ala Gln Lys His Val Ser Phe Thr Pro Gly Asp Asp Val Pro Arg
    1625                1630                1635

Val Tyr Cys Val Glu Gly Thr Pro Ile Asn Phe Ser Thr Ala Thr
    1640                1645                1650

Ser Leu Ser Asp Leu Thr Ile Glu Ser Pro Pro Asn Glu Leu Ala
    1655                1660                1665

Thr Gly Asp Gly Val Arg Ala Gly Ile Gln Ser Gly Glu Phe Glu
    1670                1675                1680

Lys Arg Asp Thr Ile Pro Thr Glu Gly Arg Ser Thr Asp Asp Ala
    1685                1690                1695

Gln Arg Gly Lys Ile Ser Ser Ile Val Thr Pro Asp Leu Asp Asp
    1700                1705                1710

Asn Lys Ala Glu Glu Gly Asp Ile Leu Ala Glu Cys Ile Asn Ser
    1715                1720                1725

Ala Met Pro Lys Gly Lys Ser His Lys Pro Phe Arg Val Lys Lys
    1730                1735                1740

Ile Met Asp Gln Val Gln Gln Ala Ser Ser Thr Ser Ser Gly Ala
    1745                1750                1755
```

-continued

```
Asn Lys Asn Gln Val Asp Thr Lys Lys Lys Pro Thr Ser Pro
    1760            1765            1770

Val Lys Pro Met Pro Gln Asn Thr Glu Tyr Arg Thr Arg Val Arg
    1775            1780            1785

Lys Asn Thr Asp Ser Lys Val Asn Val Asn Thr Glu Glu Thr Phe
    1790            1795            1800

Ser Asp Asn Lys Asp Ser Lys Lys Pro Ser Leu Gln Thr Asn Ala
    1805            1810            1815

Lys Ala Phe Asn Glu Lys Leu Pro Asn Asn Glu Asp Arg Val Arg
    1820            1825            1830

Gly Ser Phe Ala Leu Asp Ser Pro His His Tyr Thr Pro Ile Glu
    1835            1840            1845

Gly Thr Pro Tyr Cys Phe Ser Arg Asn Asp Ser Leu Ser Ser Leu
    1850            1855            1860

Asp Phe Asp Asp Asp Val Asp Leu Ser Arg Glu Lys Ala Glu
    1865            1870            1875

Leu Arg Lys Gly Lys Glu Ser Lys Asp Ser Glu Ala Lys Val Thr
    1880            1885            1890

Cys Arg Pro Glu Pro Asn Ser Ser Gln Gln Ala Ala Ser Lys Ser
    1895            1900            1905

Gln Ala Ser Ile Lys His Pro Ala Asn Arg Ala Gln Ser Lys Pro
    1910            1915            1920

Val Leu Gln Lys Gln Pro Thr Phe Pro Gln Ser Ser Lys Asp Gly
    1925            1930            1935

Pro Asp Arg Gly Ala Ala Thr Asp Glu Lys Leu Gln Asn Phe Ala
    1940            1945            1950

Ile Glu Asn Thr Pro Val Cys Phe Ser Arg Asn Ser Ser Leu Ser
    1955            1960            1965

Ser Leu Ser Asp Ile Asp Gln Glu Asn Asn Asn Lys Glu Ser
    1970            1975            1980

Glu Pro Ile Lys Glu Ala Glu Pro Ala Asn Ser Gln Gly Glu Pro
    1985            1990            1995

Ser Lys Pro Gln Ala Ser Gly Tyr Ala Pro Lys Ser Phe His Val
    2000            2005            2010

Glu Asp Thr Pro Val Cys Phe Ser Arg Asn Ser Ser Leu Ser Ser
    2015            2020            2025

Leu Ser Ile Asp Ser Glu Asp Asp Leu Leu Gln Glu Cys Ile Ser
    2030            2035            2040

Ser Ala Met Pro Lys Lys Lys Arg Pro Ser Arg Leu Lys Ser Glu
    2045            2050            2055

Ser Glu Lys Gln Ser Pro Arg Lys Val Gly Gly Ile Leu Ala Glu
    2060            2065            2070

Asp Leu Thr Leu Asp Leu Lys Asp Leu Gln Arg Pro Asp Ser Glu
    2075            2080            2085

His Ala Phe Ser Pro Asp Ser Glu Asn Phe Asp Trp Lys Ala Ile
    2090            2095            2100

Gln Glu Gly Ala Asn Ser Ile Val Ser Ser Leu His Gln Ala Ala
    2105            2110            2115

Ala Ala Ala Ala Cys Leu Ser Arg Gln Ala Ser Ser Asp Ser Asp
    2120            2125            2130

Ser Ile Leu Ser Leu Lys Ser Gly Ile Ser Leu Gly Ser Pro Phe
    2135            2140            2145
```

-continued

```
His Leu Thr Pro Asp Gln Glu  Glu Lys Pro Phe Thr  Ser Asn Lys
    2150             2155              2160

Gly Pro Arg Ile Leu Lys Pro  Gly Glu Lys Ser Thr  Leu Glu Ala
    2165             2170              2175

Lys Lys Ile Glu Ser Glu Asn  Lys Gly Ile Lys Gly  Gly Lys Lys
    2180             2185              2190

Val Tyr Lys Ser Leu Ile Thr  Gly Lys Ile Arg Ser  Asn Ser Glu
    2195             2200              2205

Ile Ser Ser Gln Met Lys Gln  Pro Leu Pro Thr Asn  Met Pro Ser
    2210             2215              2220

Ile Ser Arg Gly Arg Thr Met  Ile His Ile Pro Gly  Leu Arg Asn
    2225             2230              2235

Ser Ser Ser Ser Thr Ser Pro  Val Ser Lys Lys Gly  Pro Pro Leu
    2240             2245              2250

Lys Thr Pro Ala Ser Lys Ser  Pro Ser Glu Gly Pro  Gly Ala Thr
    2255             2260              2265

Thr Ser Pro Arg Gly Thr Lys  Pro Ala Gly Lys Ser  Glu Leu Ser
    2270             2275              2280

Pro Ile Thr Arg Gln Thr Ser  Gln Ile Ser Gly Ser  Asn Lys Gly
    2285             2290              2295

Ser Ser Arg Ser Gly Ser Arg  Asp Ser Thr Pro Ser  Arg Pro Thr
    2300             2305              2310

Gln Gln Pro Leu Ser Arg Pro  Met Gln Ser Pro Gly  Arg Asn Ser
    2315             2320              2325

Ile Ser Pro Gly Arg Asn Gly  Ile Ser Pro Pro Asn  Lys Leu Ser
    2330             2335              2340

Gln Leu Pro Arg Thr Ser Ser  Pro Ser Thr Ala Ser  Thr Lys Ser
    2345             2350              2355

Ser Gly Ser Gly Lys Met Ser  Tyr Thr Ser Pro Gly  Arg Gln Leu
    2360             2365              2370

Ser Gln Gln Asn Leu Thr Lys  Gln Ala Ser Leu Ser  Lys Asn Ala
    2375             2380              2385

Ser Ser Ile Pro Arg Ser Glu  Ser Ala Ser Lys Gly  Leu Asn Gln
    2390             2395              2400

Met Ser Asn Gly Asn Gly Ser  Asn Lys Lys Val Glu  Leu Ser Arg
    2405             2410              2415

Met Ser Ser Thr Lys Ser Ser  Gly Ser Glu Ser Asp  Arg Ser Glu
    2420             2425              2430

Arg Pro Ala Leu Val Arg Gln  Ser Thr Phe Ile Lys  Glu Ala Pro
    2435             2440              2445

Ser Pro Thr Leu Arg Arg Lys  Leu Glu Glu Ser Ala  Ser Phe Glu
    2450             2455              2460

Ser Leu Ser Pro Ser Ser Arg  Pro Asp Ser Pro Thr  Arg Ser Gln
    2465             2470              2475

Ala Gln Thr Pro Val Leu Ser  Pro Ser Leu Pro Asp  Met Ser Leu
    2480             2485              2490

Ser Thr His Pro Ser Val Gln  Ala Gly Gly Trp Arg  Lys Leu Pro
    2495             2500              2505

Pro Asn Leu Ser Pro Thr Ile  Glu Tyr Asn Asp Gly  Arg Pro Thr
    2510             2515              2520

Lys Arg His Asp Ile Ala Arg  Ser His Ser Glu Ser  Pro Ser Arg
    2525             2530              2535

Leu Pro Ile Asn Arg Ala Gly  Thr Trp Lys Arg Glu  His Ser Lys
```

```
                2540                2545                2550
His Ser  Ser Ser Leu Pro Arg  Val Ser Thr Trp Arg  Arg Thr Gly
    2555                2560                2565

Ser Ser  Ser Ser Ile Leu Ser  Ala Ser Ser Glu Ser  Ser Glu Lys
    2570                2575                2580

Ala Lys  Ser Glu Asp Glu Arg  His Val Ser Ser Met  Pro Ala Pro
    2585                2590                2595

Arg Gln  Met Lys Glu Asn Gln  Val Pro Thr Lys Gly  Thr Trp Arg
    2600                2605                2610

Lys Ile  Lys Glu Ser Asp Ile  Ser Pro Thr Gly Met  Ala Ser Gln
    2615                2620                2625

Ser Ala  Ser Ser Gly Ala Ala  Ser Gly Ala Glu Ser  Lys Pro Leu
    2630                2635                2640

Ile Tyr  Gln Met Ala Pro Pro  Val Ser Lys Thr Glu  Asp Val Trp
    2645                2650                2655

Val Arg  Ile Glu Asp Cys Pro  Ile Asn Asn Pro Arg  Ser Gly Arg
    2660                2665                2670

Ser Pro  Thr Gly Asn Thr Pro  Pro Val Ile Asp Ser  Val Ser Glu
    2675                2680                2685

Lys Gly  Ser Ser Ser Ile Lys  Asp Ser Lys Asp Thr  His Gly Lys
    2690                2695                2700

Gln Ser  Val Gly Ser Gly Ser  Pro Val Gln Thr Val  Gly Leu Glu
    2705                2710                2715

Thr Arg  Leu Asn Ser Phe Val  Gln Val Glu Ala Pro  Glu Gln Lys
    2720                2725                2730

Gly Thr  Glu Ala Lys Pro Gly  Gln Ser Asn Pro Val  Ser Ile Ala
    2735                2740                2745

Glu Thr  Ala Glu Thr Cys Ile  Ala Glu Arg Thr Pro  Phe Ser Ser
    2750                2755                2760

Ser Ser  Ser Ser Lys His Ser  Ser Pro Ser Gly Thr  Val Ala Ala
    2765                2770                2775

Arg Val  Thr Pro Phe Asn Tyr  Asn Pro Ser Pro Arg  Lys Ser Ser
    2780                2785                2790

Ala Asp  Ser Thr Ser Ala Arg  Pro Ser Gln Ile Pro  Thr Pro Val
    2795                2800                2805

Ser Thr  Asn Thr Lys Lys Arg  Asp Ser Lys Thr Asp  Ser Thr Glu
    2810                2815                2820

Ser Ser  Gly Ala Gln Ser Pro  Lys Arg His Ser Gly  Ser Tyr Leu
    2825                2830                2835

Val Thr  Ser Val
    2840

<210> SEQ ID NO 3
<211> LENGTH: 576
<212> TYPE: DNA
<213> ORGANISM: Mus musculus

<400> SEQUENCE: 3
atgactgagt ataaacttgt ggtggttgga gctggtggcg taggcaagag cgccttgacg    60
atacagctaa ttcagaatca ctttgtggat gagtatgacc ctacgataga ggactcctac   120
aggaaacaag tagtaattga tggagaaacc tgtctcttgg atattctcga cacagcaggt   180
caagaggagt acagtgcaat gagggaccag tacatgagaa ctggggaggg ctttctttgt   240
gtatttgcca taaataatac taaatcattt gaagatattc accattatag agaacaaatt   300
```

```
aaaagagtaa aggactctga agatgtgcct atggtcctgg tagggaataa gtgtgatttg    360
ccttctagaa cagtagacac gaaacaggct caggagttag caaggagtta cgggattccg    420
ttcattgaga cctcagcaaa gacaagacag ggtgttgacg atgccttcta tacattagtc    480
cgagaaattc gaaaacataa agaaaagatg agcaaagatg gaagaagaa gaagaagaag     540 tcaaggacaa ggtgtacagt tatgtgaata ctttgt                              576
```

<210> SEQ ID NO 4
<211> LENGTH: 188
<212> TYPE: PRT
<213> ORGANISM: Mus musculus

<400> SEQUENCE: 4

```
Met Thr Glu Tyr Lys Leu Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
            115                 120                 125

Gln Ala Gln Glu Leu Ala Arg Ser Tyr Gly Ile Pro Phe Ile Glu Thr
        130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Arg Thr Arg Cys Thr Val Met
                180                 185
```

<210> SEQ ID NO 5
<211> LENGTH: 1146
<212> TYPE: DNA
<213> ORGANISM: Mus musculus

<400> SEQUENCE: 5

```
atgactgcca tggaggagtc acagtcggat atcagcctcg agctccctct gagccaggag    60
acattttcag gcttatggaa actacttcct ccagaagata tcctgccatc acctcactgc    120
atggacgatc tgttgctgcc ccaggatgtt gaggagtttt tgaaggccc aagtgaagcc     180 ctccgagtgt caggagctcc tgcagcacag gaccctgtca ccgagacccc tgggccagtg    240 gccccctgccc cagccactcc atggcccctg tcatcttttg tcccttctca aaaaacttac   300
cagggcaact atggcttcca cctgggcttc ctgcagtctg gacagccaa gtctgttatg    360 tgcacgtact ctcctccccct caataagcta ttctgccagc tggcgaagac gtgcctgtg    420 cagttgtggg tcagcgccac acctccagct gggagccgtg tccgcgccat ggccatctac    480
```

-continued

```
aagaagtcac agcacatgac ggaggtcgtg agacgctgcc cccaccatga gcgctgctcc    540
gatggtgatg gcctggctcc tccccagcat cttatccggg tggaaggaaa tttgtatccc    600
gagtatctgg aagacaggca gacttttcgc cacagcgtgg tggtacctta tgagccaccc    660
gaggccggct ctgagtatac caccatccac tacaagtaca tgtgtaatag ctcctgcatg    720
gggggcatga accgccgacc tatccttacc atcatcacac tggaagactc cagtgggaac    780
cttctgggac gggacagctt tgaggttcgt gtttgtgcct gccctgggag agaccgccgt    840
acagaagaag aaaatttccg caaaaaggaa gtcctttgcc ctgaactgcc cccagggagc    900
gcaaagagag cgctgcccac ctgcacaagc gcctctcccc cgcaaaagaa aaaaccactt    960
gatggagagt atttcaccct caagatccgc gggcgtaaac gcttcgagat gttccgggag    1020
ctgaatgagg ccttagagtt aaaggatgcc catgctacag aggagtctgg agacagcagg    1080
gctcactcca gcctccagcc tagagccttc caagccttga tcaaggagga aagcccaaac    1140
tgctag                                                               1146
```

<210> SEQ ID NO 6
<211> LENGTH: 381
<212> TYPE: PRT
<213> ORGANISM: Mus musculus

<400> SEQUENCE: 6

```
Met Thr Ala Met Glu Glu Ser Gln Ser Asp Ile Ser Leu Glu Leu Pro
1               5                   10                  15

Leu Ser Gln Glu Thr Phe Ser Gly Leu Trp Lys Leu Leu Pro Pro Glu
            20                  25                  30

Asp Ile Leu Pro Ser Pro His Cys Met Asp Asp Leu Leu Leu Pro Gln
        35                  40                  45

Asp Val Glu Glu Phe Phe Glu Gly Pro Ser Glu Ala Leu Arg Val Ser
    50                  55                  60

Gly Ala Pro Ala Ala Gln Asp Pro Val Thr Glu Thr Pro Gly Pro Val
65                  70                  75                  80

Ala Pro Ala Pro Ala Thr Pro Trp Pro Leu Ser Ser Phe Val Pro Ser
                85                  90                  95

Gln Lys Thr Tyr Gln Gly Asn Tyr Gly Phe His Leu Gly Phe Leu Gln
            100                 105                 110

Ser Gly Thr Ala Lys Ser Val Met Cys Thr Tyr Ser Pro Pro Leu Asn
        115                 120                 125

Lys Leu Phe Cys Gln Leu Ala Lys Thr Cys Pro Val Gln Leu Trp Val
    130                 135                 140

Ser Ala Thr Pro Pro Ala Gly Ser Arg Val Arg Ala Met Ala Ile Tyr
145                 150                 155                 160

Lys Lys Ser Gln His Met Thr Glu Val Val Arg Cys Pro His His
                165                 170                 175

Glu Arg Cys Ser Asp Gly Asp Gly Leu Ala Pro Pro Gln His Leu Ile
            180                 185                 190

Arg Val Glu Gly Asn Leu Tyr Pro Glu Tyr Leu Glu Asp Arg Gln Thr
        195                 200                 205

Phe Arg His Ser Val Val Val Pro Tyr Glu Pro Pro Glu Ala Gly Ser
    210                 215                 220

Glu Tyr Thr Thr Ile His Tyr Lys Tyr Met Cys Asn Ser Ser Cys Met
225                 230                 235                 240

Gly Gly Met Asn Arg Arg Pro Ile Leu Thr Ile Ile Thr Leu Glu Asp
                245                 250                 255
```

```
Ser Ser Gly Asn Leu Leu Gly Arg Asp Ser Phe Glu Val Arg Val Cys
            260                 265                 270

Ala Cys Pro Gly Arg Asp Arg Arg Thr Glu Glu Glu Asn Phe Arg Lys
        275                 280                 285

Lys Glu Val Leu Cys Pro Glu Leu Pro Pro Gly Ser Ala Lys Arg Ala
    290                 295                 300

Leu Pro Thr Cys Thr Ser Ala Ser Pro Pro Gln Lys Lys Pro Leu
305                 310                 315                 320

Asp Gly Glu Tyr Phe Thr Leu Lys Ile Arg Gly Arg Lys Arg Phe Glu
                325                 330                 335

Met Phe Arg Glu Leu Asn Glu Ala Leu Glu Leu Lys Asp Ala His Ala
            340                 345                 350

Thr Glu Glu Ser Gly Asp Ser Arg Ala His Ser Ser Leu Gln Pro Arg
        355                 360                 365

Ala Phe Gln Ala Leu Ile Lys Glu Glu Ser Pro Asn Cys
    370                 375                 380
```

<210> SEQ ID NO 7
<211> LENGTH: 1173
<212> TYPE: DNA
<213> ORGANISM: Mus musculus

<400> SEQUENCE: 7

```
atgactgcca tggaggagtc acagtcggat atcagcctcg agctccctct gagccaggag    60
acattttcag gcttatggaa actacttcct ccagaagata tcctgccatc acctcactgc   120
atggacgatc tgttgctgcc ccaggatgtt gaggagtttt ttgaaggccc aagtgaagcc   180
ctccgagtgt caggagctcc tgcagcacag gaccctgtca ccgagacccc tgggccagtg   240
gcccctgccc cagccactcc atggcccctg tcatctttg tcccttctca aaaaacttac    300
cagggcaact atggcttcca cctgggcttc ctgcagtctg ggacagccaa gtctgttatg   360
tgcacgtact ctcctcccct caataagcta ttctgccagc tggcgaagac gtgccctgtg   420
cagttgtggg tcagcgccac acctccagct gggagccgtg tccgcgccat ggccatctac   480
aagaagtcac agcacatgac ggaggtcgtg agacgctgcc cccaccatga gcgctgctcc   540
gatggtgatg gcctggctcc tccccagcat cttatccggg tggaaggaaa tttgtatccc   600
gagtatctgg aagacaggca acttttcgc cacagcgtgg tggtacctta tgagccaccc    660
gaggccggct ctgagtatac caccatccac tacaagtaca tgtgtaatag ctcctgcatg   720
gggggcatga accgccgacc tatccttacc atcatcacac tggaagactc cagtgggaac   780
cttctgggac gggacagctt tgaggttcgt gtttgtgcct gccctgggag agaccgccgt   840
acagaagaag aaaatttccg caaaaaggaa gtcctttgcc ctgaactgcc ccagggagc    900
gcaaagagag cgctgcccac ctgcacaagc gcctctcccc gcaaaagaa aaaccactt    960
gatggagagt atttcaccct caagatccgc gggcgtaaac gcttcgagat gttccgggag  1020
ctgaatgagg ccttagagtt aaaggatgcc catgctacag aggagtctgg agacagcagg  1080
gctcactcca gctacctgaa gaccaagaag ggccagtcta cttcccgcca taaaaaaaca  1140
atggtcaaga aagtggggcc tgactcagac tga                               1173
```

<210> SEQ ID NO 8
<211> LENGTH: 390
<212> TYPE: PRT
<213> ORGANISM: Mus musculus

<400> SEQUENCE: 8

```
Met Thr Ala Met Glu Glu Ser Gln Ser Asp Ile Ser Leu Glu Leu Pro
1               5                   10                  15

Leu Ser Gln Glu Thr Phe Ser Gly Leu Trp Lys Leu Leu Pro Pro Glu
                20                  25                  30

Asp Ile Leu Pro Ser Pro His Cys Met Asp Asp Leu Leu Leu Pro Gln
            35                  40                  45

Asp Val Glu Glu Phe Phe Glu Gly Pro Ser Glu Ala Leu Arg Val Ser
        50                  55                  60

Gly Ala Pro Ala Ala Gln Asp Pro Val Thr Glu Thr Pro Gly Pro Val
65                  70                  75                  80

Ala Pro Ala Pro Ala Thr Pro Trp Pro Leu Ser Ser Phe Val Pro Ser
                85                  90                  95

Gln Lys Thr Tyr Gln Gly Asn Tyr Gly Phe His Leu Gly Phe Leu Gln
            100                 105                 110

Ser Gly Thr Ala Lys Ser Val Met Cys Thr Tyr Ser Pro Pro Leu Asn
        115                 120                 125

Lys Leu Phe Cys Gln Leu Ala Lys Thr Cys Pro Val Gln Leu Trp Val
130                 135                 140

Ser Ala Thr Pro Pro Ala Gly Ser Arg Val Arg Ala Met Ala Ile Tyr
145                 150                 155                 160

Lys Lys Ser Gln His Met Thr Glu Val Val Arg Arg Cys Pro His His
                165                 170                 175

Glu Arg Cys Ser Asp Gly Asp Gly Leu Ala Pro Pro Gln His Leu Ile
            180                 185                 190

Arg Val Glu Gly Asn Leu Tyr Pro Glu Tyr Leu Glu Asp Arg Gln Thr
        195                 200                 205

Phe Arg His Ser Val Val Val Pro Tyr Glu Pro Pro Glu Ala Gly Ser
210                 215                 220

Glu Tyr Thr Thr Ile His Tyr Lys Tyr Met Cys Asn Ser Ser Cys Met
225                 230                 235                 240

Gly Gly Met Asn Arg Arg Pro Ile Leu Thr Ile Ile Thr Leu Glu Asp
                245                 250                 255

Ser Ser Gly Asn Leu Leu Gly Arg Asp Ser Phe Glu Val Arg Val Cys
            260                 265                 270

Ala Cys Pro Gly Arg Asp Arg Arg Thr Glu Glu Glu Asn Phe Arg Lys
        275                 280                 285

Lys Glu Val Leu Cys Pro Glu Leu Pro Pro Gly Ser Ala Lys Arg Ala
290                 295                 300

Leu Pro Thr Cys Thr Ser Ala Ser Pro Pro Gln Lys Lys Lys Pro Leu
305                 310                 315                 320

Asp Gly Glu Tyr Phe Thr Leu Lys Ile Arg Gly Arg Lys Arg Phe Glu
                325                 330                 335

Met Phe Arg Glu Leu Asn Glu Ala Leu Glu Leu Lys Asp Ala His Ala
            340                 345                 350

Thr Glu Glu Ser Gly Asp Ser Arg Ala His Ser Ser Tyr Leu Lys Thr
        355                 360                 365

Lys Lys Gly Gln Ser Thr Ser Arg His Lys Lys Thr Met Val Lys Lys
370                 375                 380

Val Gly Pro Asp Ser Asp
385                 390
```

<210> SEQ ID NO 9

<211> LENGTH: 1779
<212> TYPE: DNA
<213> ORGANISM: Mus musculus

<400> SEQUENCE: 9

```
atgggtcggg ggctgctccg gggcctgtgg ccgctgcata tcgtcctgtg gacgcgcatc      60
gccagcacga tcccgccgca cgttcccaag tcggatgtgg aaatggaagc cagaaagat     120
gcatccatcc acctaagctg taataggacc atccatccac tgaaacattt taacagtgat     180
gtcatggcca gcgacaatgg cggtgcggtc aagcttccac agctgtgcaa gttttgcgat     240
gtgagactgt ccacttgcga caaccagaag tcctgcatga gcaactgcag catcacggcc     300
atctgtgaga agccgcatga agtctgcgtg gccgtgtgga ggaagaacga caagaacatt     360
actctggaga cggtttgcca cgaccccaag ctcacctacc acggcttcac tctggaagat     420
gccgcttctc ccaagtgtgt catgaaggaa aagaaaaggg cgggcgagac tttcttcatg     480
tgtgcctgta acatggaaga gtgcaacgat tacatcatct tttcggaaga atacaccacc     540
agcagtcccg acctgttgtt ggtcattatc caagtgacgg tgtcagcct cctgcctccg     600
ctggggattg ccatagctgt catcatcatc ttctactgct accgtgtcca ccggcagcag     660
aagctgagcc cgtcctggga gagcagcaag ccccggaaac tgatggattt cagtgacaat     720
tgtgccatca tcctggagga cgaccgctcc gacatcagct ccacgtgcgc caacaacatc     780
aaccacaaca cggagctgct gcccatcgag ctggacacgc tggtggggaa gggccgcttc     840
gccgaggtct acaaggccaa gctgaagcag aacacctcag agcagtttga ccgtggct     900
gtcaagatct tcccctacga ggagtactcc tcgtggaaaa cagagaagga catcttctcc     960
gatatcaacc tgaagcatga gaacatcctg cagttcctga cggccgagga gcggaagaca   1020
gagctgggca gcagtactg gctgatcacg gcgttccacg cgaagggcaa cctgcaggag   1080
tacctcacga ggcatgtcat cagctgggag gacctgagga gctgggcag ctccctggcc   1140
cggggcatcg ctcatctcca cagtgaccac actccttgtg ggaggcccaa gatgcccatt   1200
gttcacaggg acctcaagag ctctaacatc ctagtgaaga cgacttgac ctgttgcctg   1260
tgtgacttcg ggctgtcctt cgcgcctggac cctactctgt ctgtggatga cctggccaac   1320
agcgggcagg tgggaacggc aagatacatg gccccggaag ttctagaatc caggatgaat   1380
ctggaaaacg tggagtcgtt caagcagacg gatgtctact ccatggctct ggtactctgg   1440
gaaatgacgt cccgctgcaa tgctgtggga gaagtgaagg attacgagcc cccatttggt   1500
tccaaggtgc gggagcaccc ctgtgtggag agcatgaaag acagtgtgct gagagaccga   1560
ggggcggccgg aaattcccag cttctggctc aaccaccagg gcatccagat cgtgtgtgag   1620
actttgaccg agtgctggga ccatgacccc gaagcccgtc tcacagcaca gtgtgtggca   1680
gagcgcttca gtgagctgga gcatccggag agactctctg ggaggagctg ctcccaggag   1740
aagattccag aagatggctc gctgaacact accaaatag                          1779
```

<210> SEQ ID NO 10
<211> LENGTH: 592
<212> TYPE: PRT
<213> ORGANISM: Mus musculus

<400> SEQUENCE: 10

```
Met Gly Arg Gly Leu Leu Arg Gly Leu Trp Pro Leu His Ile Val Leu
1               5                   10                  15

Trp Thr Arg Ile Ala Ser Thr Ile Pro Pro His Val Pro Lys Ser Asp
            20                  25                  30
```

```
Val Glu Met Glu Ala Gln Lys Asp Ala Ser Ile His Leu Ser Cys Asn
            35                  40                  45

Arg Thr Ile His Pro Leu Lys His Phe Asn Ser Asp Val Met Ala Ser
     50                  55                  60

Asp Asn Gly Gly Ala Val Lys Leu Pro Gln Leu Cys Lys Phe Cys Asp
 65                  70                  75                  80

Val Arg Leu Ser Thr Cys Asp Asn Gln Lys Ser Cys Met Ser Asn Cys
                 85                  90                  95

Ser Ile Thr Ala Ile Cys Glu Lys Pro His Glu Val Cys Val Ala Val
            100                 105                 110

Trp Arg Lys Asn Asp Lys Asn Ile Thr Leu Glu Thr Val Cys His Asp
            115                 120                 125

Pro Lys Leu Thr Tyr His Gly Phe Thr Leu Glu Asp Ala Ala Ser Pro
            130                 135                 140

Lys Cys Val Met Lys Glu Lys Lys Arg Ala Gly Glu Thr Phe Phe Met
145                 150                 155                 160

Cys Ala Cys Asn Met Glu Glu Cys Asn Asp Tyr Ile Ile Phe Ser Glu
                165                 170                 175

Glu Tyr Thr Thr Ser Ser Pro Asp Leu Leu Leu Val Ile Ile Gln Val
            180                 185                 190

Thr Gly Val Ser Leu Leu Pro Pro Leu Gly Ile Ala Ile Ala Val Ile
            195                 200                 205

Ile Ile Phe Tyr Cys Tyr Arg Val His Arg Gln Gln Lys Leu Ser Pro
210                 215                 220

Ser Trp Glu Ser Ser Lys Pro Arg Lys Leu Met Asp Phe Ser Asp Asn
225                 230                 235                 240

Cys Ala Ile Ile Leu Glu Asp Asp Arg Ser Asp Ile Ser Ser Thr Cys
                245                 250                 255

Ala Asn Asn Ile Asn His Asn Thr Glu Leu Leu Pro Ile Glu Leu Asp
                260                 265                 270

Thr Leu Val Gly Lys Gly Arg Phe Ala Glu Val Tyr Lys Ala Lys Leu
            275                 280                 285

Lys Gln Asn Thr Ser Glu Gln Phe Glu Thr Val Ala Val Lys Ile Phe
            290                 295                 300

Pro Tyr Glu Glu Tyr Ser Ser Trp Lys Thr Glu Lys Asp Ile Phe Ser
305                 310                 315                 320

Asp Ile Asn Leu Lys His Glu Asn Ile Leu Gln Phe Leu Thr Ala Glu
                325                 330                 335

Glu Arg Lys Thr Glu Leu Gly Lys Gln Tyr Trp Leu Ile Thr Ala Phe
            340                 345                 350

His Ala Lys Gly Asn Leu Gln Glu Tyr Leu Thr Arg His Val Ile Ser
            355                 360                 365

Trp Glu Asp Leu Arg Lys Leu Gly Ser Ser Leu Ala Arg Gly Ile Ala
            370                 375                 380

His Leu His Ser Asp His Thr Pro Cys Gly Arg Pro Lys Met Pro Ile
385                 390                 395                 400

Val His Arg Asp Leu Lys Ser Ser Asn Ile Leu Val Lys Asn Asp Leu
                405                 410                 415

Thr Cys Cys Leu Cys Asp Phe Gly Leu Ser Leu Arg Leu Asp Pro Thr
                420                 425                 430

Leu Ser Val Asp Asp Leu Ala Asn Ser Gly Gln Val Gly Thr Ala Arg
            435                 440                 445
```

```
Tyr Met Ala Pro Glu Val Leu Glu Ser Arg Met Asn Leu Glu Asn Val
    450                 455                 460
Glu Ser Phe Lys Gln Thr Asp Val Tyr Ser Met Ala Leu Val Leu Trp
465                 470                 475                 480
Glu Met Thr Ser Arg Cys Asn Ala Val Gly Glu Val Lys Asp Tyr Glu
                485                 490                 495
Pro Pro Phe Gly Ser Lys Val Arg Glu His Pro Cys Val Glu Ser Met
            500                 505                 510
Lys Asp Ser Val Leu Arg Asp Arg Gly Arg Pro Glu Ile Pro Ser Phe
        515                 520                 525
Trp Leu Asn His Gln Gly Ile Gln Ile Val Cys Glu Thr Leu Thr Glu
    530                 535                 540
Cys Trp Asp His Asp Pro Glu Ala Arg Leu Thr Ala Gln Cys Val Ala
545                 550                 555                 560
Glu Arg Phe Ser Glu Leu Glu His Pro Glu Arg Leu Ser Gly Arg Ser
                565                 570                 575
Cys Ser Gln Glu Lys Ile Pro Glu Asp Gly Ser Leu Asn Thr Thr Lys
            580                 585                 590

<210> SEQ ID NO 11
<211> LENGTH: 1704
<212> TYPE: DNA
<213> ORGANISM: Mus musculus

<400> SEQUENCE: 11
atgggtcggg ggctgctccg gggcctgtgg ccgctgcata tcgtcctgtg gacgcgcatc      60
gccagcacga tcccgccgca cgttcccaag tcggttaaca gtgatgtcat ggccagcgac     120
aatggcggtg cggtcaagct tccacagctg tgcaagtttt gcgatgtgag actgtccact     180
tgcgacaacc agaagtcctg catgagcaac tgcagcatca cggccatctg tgagaagccg     240
catgaagtct gcgtggccgt gtggaggaag aacgacaaga acattactct ggagacggtt     300
tgccacgacc ccaagctcac ctaccacggc ttcactctgg aagatgccgc ttctcccaag     360
tgtgtcatga ggaaaagaa aagggcgggc gagactttct tcatgtgtgc ctgtaacatg     420
gaagagtgca acgattacat catcttttcg gaagaataca ccaccagcag tcccgacctg     480
ttgttggtca ttatccaagt gacgggtgtc agcctcctgc tccgctgggg gattgccata     540
gctgtcatca tcatcttcta ctgctaccgt gtccaccggc agcagaagct gagcccgtcc     600
tgggagagca gcaagcccgg aaactgatg gatttcagtg acaattgtgc catcatcctg     660
gaggacgacc gctccgacat cagctccacg tgcgccaaca acatcaacca aacacggag      720 ctgctgccca tcgagctgga cacgctggtg ggaagggcc gcttcgccga ggtctacaag     780
gccaagctga gcagaacac tcagagcag tttgagaccg tggctgtcaa gatcttcccc     840
tacgaggagt actcctcgtg gaaaacagag aaggacatct tctccgatat caacctgaag     900
catgagaaca tcctgcagtt cctgacggcc gaggagcgga gacagagct gggcaagcag     960 tactggctga tcacggcgtt ccacgcgaag ggcaacctgc aggagtacct cacgaggcat    1020
gtcatcagct gggaggacct gaggaagctg ggcagctccc tggcccgggg catcgctcat    1080
ctccacagtg accacactcc ttgtgggagg cccaagatgc ccattgttca cagggaccct    1140
aagagctcta acatcctagt gaagaacgac ttgacctgtt gcctgtgtga cttcgggctg    1200
tccttgcgcc tggaccctac tctgtctgtg gatgacctgg ccaacagcgg gcaggtggga    1260
acggcaagat acatggcccc ggaagttcta gaatccagga tgaatctgga aaacgtggag    1320
```

```
tcgttcaagc agacggatgt ctactccatg gctctggtac tctgggaaat gacgtcccgc   1380
tgcaatgctg tgggagaagt gaaggattac gagcccccat ttggttccaa ggtgcgggag   1440 caccectgtg tggagagcat gaaagacagt gtgctgagag accgagggcg gccggaaatt   1500
cccagcttct ggctcaacca ccagggcatc cagatcgtgt gtgagacttt gaccgagtgc   1560
tgggaccatg accccgaagc ccgtctcaca gcacagtgtg tggcagagcg cttcagtgag   1620
ctggagcatc cggagagact ctctgggagg agctgctccc aggagaagat tccagaagat   1680
ggctcgctga acactaccaa atag                                          1704
```

<210> SEQ ID NO 12
<211> LENGTH: 567
<212> TYPE: PRT
<213> ORGANISM: Mus musculus

<400> SEQUENCE: 12

```
Met Gly Arg Gly Leu Leu Arg Gly Leu Trp Pro Leu His Ile Val Leu
1               5                   10                  15

Trp Thr Arg Ile Ala Ser Thr Ile Pro Pro His Val Pro Lys Ser Val
            20                  25                  30

Asn Ser Asp Val Met Ala Ser Asp Asn Gly Gly Ala Val Lys Leu Pro
        35                  40                  45

Gln Leu Cys Lys Phe Cys Asp Val Arg Leu Ser Thr Cys Asp Asn Gln
    50                  55                  60

Lys Ser Cys Met Ser Asn Cys Ser Ile Thr Ala Ile Cys Glu Lys Pro
65                  70                  75                  80

His Glu Val Cys Val Ala Val Trp Arg Lys Asn Asp Lys Asn Ile Thr
                85                  90                  95

Leu Glu Thr Val Cys His Asp Pro Lys Leu Thr Tyr His Gly Phe Thr
            100                 105                 110

Leu Glu Asp Ala Ala Ser Pro Lys Cys Val Met Lys Glu Lys Lys Arg
        115                 120                 125

Ala Gly Glu Thr Phe Phe Met Cys Ala Cys Asn Met Glu Glu Cys Asn
    130                 135                 140

Asp Tyr Ile Ile Phe Ser Glu Glu Tyr Thr Thr Ser Ser Pro Asp Leu
145                 150                 155                 160

Leu Leu Val Ile Ile Gln Val Thr Gly Val Ser Leu Leu Pro Pro Leu
                165                 170                 175

Gly Ile Ala Ile Ala Val Ile Ile Phe Tyr Cys Tyr Arg Val His
            180                 185                 190

Arg Gln Gln Lys Leu Ser Pro Ser Trp Glu Ser Ser Lys Pro Arg Lys
        195                 200                 205

Leu Met Asp Phe Ser Asp Asn Cys Ala Ile Leu Glu Asp Asp Arg
    210                 215                 220

Ser Asp Ile Ser Ser Thr Cys Ala Asn Asn Ile Asn His Asn Thr Glu
225                 230                 235                 240

Leu Leu Pro Ile Glu Leu Asp Thr Leu Val Gly Lys Gly Arg Phe Ala
                245                 250                 255

Glu Val Tyr Lys Ala Lys Leu Lys Gln Asn Thr Ser Glu Gln Phe Glu
            260                 265                 270

Thr Val Ala Val Lys Ile Phe Pro Tyr Glu Glu Tyr Ser Ser Trp Lys
        275                 280                 285

Thr Glu Lys Asp Ile Phe Ser Asp Ile Asn Leu Lys His Glu Asn Ile
    290                 295                 300
```

```
Leu Gln Phe Leu Thr Ala Glu Glu Arg Lys Thr Glu Leu Gly Lys Gln
305                 310                 315                 320
Tyr Trp Leu Ile Thr Ala Phe His Ala Lys Gly Asn Leu Gln Glu Tyr
                325                 330                 335
Leu Thr Arg His Val Ile Ser Trp Glu Asp Leu Arg Lys Leu Gly Ser
            340                 345                 350
Ser Leu Ala Arg Gly Ile Ala His Leu His Ser Asp His Thr Pro Cys
        355                 360                 365
Gly Arg Pro Lys Met Pro Ile Val His Arg Asp Leu Lys Ser Ser Asn
    370                 375                 380
Ile Leu Val Lys Asn Asp Leu Thr Cys Cys Leu Cys Asp Phe Gly Leu
385                 390                 395                 400
Ser Leu Arg Leu Asp Pro Thr Leu Ser Val Asp Asp Leu Ala Asn Ser
                405                 410                 415
Gly Gln Val Gly Thr Ala Arg Tyr Met Ala Pro Glu Val Leu Glu Ser
            420                 425                 430
Arg Met Asn Leu Glu Asn Val Glu Ser Phe Lys Gln Thr Asp Val Tyr
        435                 440                 445
Ser Met Ala Leu Val Leu Trp Glu Met Thr Ser Arg Cys Asn Ala Val
    450                 455                 460
Gly Glu Val Lys Asp Tyr Glu Pro Pro Phe Gly Ser Lys Val Arg Glu
465                 470                 475                 480
His Pro Cys Val Glu Ser Met Lys Asp Ser Val Leu Arg Asp Arg Gly
                485                 490                 495
Arg Pro Glu Ile Pro Ser Phe Trp Leu Asn His Gln Gly Ile Gln Ile
            500                 505                 510
Val Cys Glu Thr Leu Thr Glu Cys Trp Asp His Asp Pro Glu Ala Arg
        515                 520                 525
Leu Thr Ala Gln Cys Val Ala Glu Arg Phe Ser Glu Leu Glu His Pro
    530                 535                 540
Glu Arg Leu Ser Gly Arg Ser Cys Ser Gln Glu Lys Ile Pro Glu Asp
545                 550                 555                 560
Gly Ser Leu Asn Thr Thr Lys
                565

<210> SEQ ID NO 13
<211> LENGTH: 1656
<212> TYPE: DNA
<213> ORGANISM: Mus musculus

<400> SEQUENCE: 13
atggacaata tgtctataac aaatacacca acaagtaacg atgcctgtct gagcattgta      60
catagtttga tgtgtcatag acaaggtggg gaaagtgaaa cctttgcaaa agagcaatt     120
gagagtttgg taagaagct gaaagagaaa aaagatgaat tggattcttt aataacagct     180
ataactacaa atggagctca tcctagcaag tgtgtcacca tacagagaac attggatgga     240
cgacttcagg tggctggtcg gaaaggattt cctcatgtga tctatgcccg tctgtggagg     300
tggcctgatc tacacaagaa tgaactaaag catgttaaat attgtcagta tgcgtttgac     360
ttaaaatgtg acagtgtctg tgtgaatcca tatcactatg agcgggttgt ctcacctgga     420
attgatctct caggattaac actgcagagt aatgctccaa gtatgttagt gaaggatgag     480
tacgttcacg actttgaagg acagccgtcc ttacccactg aaggacattc gattcaaacc     540
atccaacacc cgccaagtaa tcgcgcatca acggagacgt acagcgcccc ggctctgtta     600
```

```
gccccggcag agtctaacgc caccagcacc accaacttcc ccaacattcc tgtggcttcc    660
acaagtcagc cggccagtat tctggcgggc agccatagtg aaggactgtt gcagatagct    720
tcagggcctc agccaggaca gcagcagaat ggatttactg ctcagccagc tacttaccat    780
cataacagca ctaccacctg gactggaagt aggactgcac catacacacc taatttgcct    840
caccaccaaa acggccatct tcagcaccac ccgcctatgc cgccccatcc tggacattac    900
tggccagttc acaatgagct tgcattccag cctcccattt ccaatcatcc tgctcctgag    960
tactggtgct ccattgctta ctttgaaatg gacgttcagg taggagagac gtttaaggtc   1020
ccttcaagct gccctgttgt gactgtggat ggctatgtgg atccttcggg aggagatcgc   1080
ttttgcttgg gtcaactctc caatgtccac aggacagaag cgattgagag agcgaggttg   1140
cacataggca aaggagtgca gttggaatgt aaaggtgaag gtgacgtttg ggtcaggtgc   1200
cttagtgacc acgcggtctt tgtacagagt tactacctgg acagagaagc tggccgagca   1260
cctggcgacg ctgttcataa gatctaccca agcgcgtata taaaggtctt tgatctgcgg   1320
cagtgtcacc ggcagatgca gcaacaggcg ccactgcgc aagctgcagc tgctgctcag   1380
gcggcggccg tggcagggaa catccctggc cctgggtccg tgggtggaat agctccagcc   1440
atcagtctgt ctgctgctgc tggcatcggt gtggatgacc tccggcgatt gtgcattctc   1500
aggatgagct ttgtgaaggg ctggggccca gactacccca ggcagagcat caaggaaacc   1560
ccgtgctgga ttgagattca ccttcaccga gctctgcagc tcttggatga agtcctgcac   1620
accatgccca ttgcggaccc acagccttta gactga                            1656
```

<210> SEQ ID NO 14
<211> LENGTH: 551
<212> TYPE: PRT
<213> ORGANISM: Mus musculus

<400> SEQUENCE: 14

Met Asp Asn Met Ser Ile Thr Asn Thr Pro Thr Ser Asn Asp Ala Cys
1               5                   10                  15

Leu Ser Ile Val His Ser Leu Met Cys His Arg Gln Gly Gly Glu Ser
            20                  25                  30

Glu Thr Phe Ala Lys Arg Ala Ile Glu Ser Leu Val Lys Lys Leu Lys
        35                  40                  45

Glu Lys Lys Asp Glu Leu Asp Ser Leu Ile Thr Ala Ile Thr Thr Asn
    50                  55                  60

Gly Ala His Pro Ser Lys Cys Val Thr Ile Gln Arg Thr Leu Asp Gly
65                  70                  75                  80

Arg Leu Gln Val Ala Gly Arg Lys Gly Phe Pro His Val Ile Tyr Ala
                85                  90                  95

Arg Leu Trp Arg Trp Pro Asp Leu His Lys Asn Glu Leu Lys His Val
            100                 105                 110

Lys Tyr Cys Gln Tyr Ala Phe Asp Leu Lys Cys Asp Ser Val Cys Val
        115                 120                 125

Asn Pro Tyr His Tyr Glu Arg Val Val Ser Pro Gly Ile Asp Leu Ser
    130                 135                 140

Gly Leu Thr Leu Gln Ser Asn Ala Pro Ser Met Leu Val Lys Asp Glu
145                 150                 155                 160

Tyr Val His Asp Phe Glu Gly Gln Pro Ser Leu Pro Thr Glu Gly His
                165                 170                 175

Ser Ile Gln Thr Ile Gln His Pro Pro Ser Asn Arg Ala Ser Thr Glu
            180                 185                 190

```
Thr Tyr Ser Ala Pro Ala Leu Leu Ala Pro Ala Glu Ser Asn Ala Thr
            195                 200                 205

Ser Thr Thr Asn Phe Pro Asn Ile Pro Val Ala Ser Thr Ser Gln Pro
        210                 215                 220

Ala Ser Ile Leu Ala Gly Ser His Ser Glu Gly Leu Leu Gln Ile Ala
225                 230                 235                 240

Ser Gly Pro Gln Pro Gly Gln Gln Gln Asn Gly Phe Thr Ala Gln Pro
                245                 250                 255

Ala Thr Tyr His His Asn Ser Thr Thr Thr Trp Thr Gly Ser Arg Thr
            260                 265                 270

Ala Pro Tyr Thr Pro Asn Leu Pro His His Gln Asn Gly His Leu Gln
        275                 280                 285

His His Pro Pro Met Pro Pro His Pro Gly His Tyr Trp Pro Val His
290                 295                 300

Asn Glu Leu Ala Phe Gln Pro Pro Ile Ser Asn His Pro Ala Pro Glu
305                 310                 315                 320

Tyr Trp Cys Ser Ile Ala Tyr Phe Glu Met Asp Val Gln Val Gly Glu
            325                 330                 335

Thr Phe Lys Val Pro Ser Ser Cys Pro Val Val Thr Val Asp Gly Tyr
        340                 345                 350

Val Asp Pro Ser Gly Gly Asp Arg Phe Cys Leu Gly Gln Leu Ser Asn
            355                 360                 365

Val His Arg Thr Glu Ala Ile Glu Arg Ala Arg Leu His Ile Gly Lys
        370                 375                 380

Gly Val Gln Leu Glu Cys Lys Gly Glu Gly Asp Val Trp Val Arg Cys
385                 390                 395                 400

Leu Ser Asp His Ala Val Phe Val Gln Ser Tyr Tyr Leu Asp Arg Glu
            405                 410                 415

Ala Gly Arg Ala Pro Gly Asp Ala Val His Lys Ile Tyr Pro Ser Ala
        420                 425                 430

Tyr Ile Lys Val Phe Asp Leu Arg Gln Cys His Arg Gln Met Gln Gln
            435                 440                 445

Gln Ala Thr Ala Gln Ala Ala Ala Ala Gln Ala Ala Ala Val
        450                 455                 460

Ala Gly Asn Ile Pro Gly Pro Gly Ser Val Gly Gly Ile Ala Pro Ala
465                 470                 475                 480

Ile Ser Leu Ser Ala Ala Gly Ile Gly Val Asp Asp Leu Arg Arg
                485                 490                 495

Leu Cys Ile Leu Arg Met Ser Phe Val Lys Gly Trp Gly Pro Asp Tyr
            500                 505                 510

Pro Arg Gln Ser Ile Lys Glu Thr Pro Cys Trp Ile Glu Ile His Leu
        515                 520                 525

His Arg Ala Leu Gln Leu Leu Asp Glu Val Leu His Thr Met Pro Ile
        530                 535                 540

Ala Asp Pro Gln Pro Leu Asp
545                 550
```